(12) United States Patent
Fago et al.

(10) Patent No.: US 10,201,352 B2
(45) Date of Patent: Feb. 12, 2019

(54) ROBOTIC ASSISTED CLIP APPLIER

(71) Applicant: AtriCure, Inc., Mason, OH (US)

(72) Inventors: Frank M. Fago, Mason, OH (US); Keith Edward Martin, Dayton, OH (US)

(73) Assignee: AtriCure, Inc., Mason, OH (US)

( * ) Notice: Subject to any disclaimer, the term of this patent is extended or adjusted under 35 U.S.C. 154(b) by 268 days.

(21) Appl. No.: 15/231,777

(22) Filed: Aug. 8, 2016

(65) Prior Publication Data

US 2018/0036007 A1 Feb. 8, 2018

(51) Int. Cl.
| | | |
|---|---|---|
| *A61B 17/128* | (2006.01) | |
| *A61B 17/122* | (2006.01) | |
| *A61B 34/30* | (2016.01) | |
| *A61B 17/00* | (2006.01) | |

(52) U.S. Cl.
CPC ........ *A61B 17/122* (2013.01); *A61B 17/1285* (2013.01); *A61B 34/30* (2016.02); *A61B 17/1227* (2013.01); *A61B 2017/0046* (2013.01); *A61B 2017/00243* (2013.01); *A61B 2017/00477* (2013.01)

(58) Field of Classification Search
CPC .............. A61B 34/30; A61B 2034/302; A61B 17/1285; A61B 17/1227; A61B 17/122; A61B 2017/00243; A61B 2017/0046; A61B 2017/00477
See application file for complete search history.

(56) References Cited

U.S. PATENT DOCUMENTS

| | | | | |
|---|---|---|---|---|
| 5,217,473 A | * | 6/1993 | Yoon ................ | A61B 17/12013 606/141 |
| 7,569,064 B1 | * | 8/2009 | Hausen ............. | A61B 17/0643 606/151 |
| 2003/0158463 A1 | * | 8/2003 | Julian .............. | A61B 17/00234 600/104 |
| 2004/0102771 A1 | * | 5/2004 | Bertolero ........... | A61B 18/1442 606/41 |
| 2005/0021061 A1 | * | 1/2005 | Dennis .............. | A61B 17/1227 606/157 |
| 2005/0149068 A1 | * | 7/2005 | Williams ............ | A61B 17/122 606/151 |
| 2005/0149069 A1 | * | 7/2005 | Bertolero ............ | A61B 1/12 606/151 |
| 2005/0277959 A1 | * | 12/2005 | Cosgrove ............ | A61B 17/12 606/151 |
| 2006/0004388 A1 | * | 1/2006 | Whayne ............. | A61B 17/0401 606/151 |
| 2006/0020271 A1 | * | 1/2006 | Stewart ............. | A61B 17/0057 606/139 |

(Continued)

*Primary Examiner* — Katrina Stransky
(74) *Attorney, Agent, or Firm* — Dorton & Willis LLP; Ryan Willis

(57) ABSTRACT

A medical instrument comprising an end effector comprising a first jaw configured to be repositionable with respect to a second jaw, the first and second jaws removably mounted to an open-ended occlusion clip, the end effector configured to configured to be removably coupled to an open-ended occlusion clip with a pair of terminal ends and first and second robotic arms, and wherein the end effector includes at least one of a cavity and a projection configured to be engaged by at least one of the first and second robotic arms.

20 Claims, 29 Drawing Sheets

(56) References Cited

U.S. PATENT DOCUMENTS

| | | | |
|---|---|---|---|
| 2007/0016228 A1* | 1/2007 | Salas | A61B 17/122 606/142 |
| 2008/0033457 A1* | 2/2008 | Francischelli | A61B 17/0057 606/142 |
| 2008/0167750 A1* | 7/2008 | Stahler | A61B 17/12122 700/245 |
| 2008/0208324 A1* | 8/2008 | Glithero | A61B 17/00491 623/1.36 |
| 2008/0243141 A1* | 10/2008 | Privitera | A61B 18/1442 606/130 |
| 2008/0294175 A1* | 11/2008 | Bardsley | A61B 17/12009 606/113 |
| 2008/0312664 A1* | 12/2008 | Bardsley | A61B 17/12009 606/142 |
| 2009/0012545 A1* | 1/2009 | Williamson, IV | A61B 17/083 606/157 |
| 2009/0209986 A1* | 8/2009 | Stewart | A61B 17/122 606/157 |
| 2010/0179570 A1* | 7/2010 | Privitera | A61B 17/122 606/142 |
| 2010/0228279 A1* | 9/2010 | Miles | A61B 17/0057 606/198 |
| 2011/0009853 A1* | 1/2011 | Bertolero | A61B 17/122 606/14 |
| 2011/0276075 A1* | 11/2011 | Fung | A61B 18/1492 606/185 |
| 2012/0035631 A1* | 2/2012 | Hughett, Sr. | A61B 17/1227 606/157 |
| 2012/0109161 A1* | 5/2012 | Privitera | A61B 17/1227 606/142 |
| 2012/0123445 A1* | 5/2012 | Hughett, Sr. | A61B 17/1227 606/142 |
| 2012/0316584 A1* | 12/2012 | Miles | A61B 17/0057 606/157 |
| 2012/0323256 A1* | 12/2012 | Privitera | A61B 18/02 606/130 |
| 2013/0131649 A1* | 5/2013 | Hughett, Sr. | A61B 17/1227 606/1 |
| 2013/0184726 A1* | 7/2013 | Weisshaupt | A61B 17/1227 606/158 |
| 2013/0190777 A1* | 7/2013 | Hughett, Sr. | A61B 17/1227 606/142 |
| 2013/0226200 A1* | 8/2013 | Kappel | A61B 17/128 606/142 |
| 2013/0282021 A1* | 10/2013 | Parihar | A61B 17/105 606/130 |
| 2014/0005696 A1* | 1/2014 | Schulz | A61B 17/1285 606/143 |
| 2014/0135793 A1* | 5/2014 | Cooper | A61B 34/30 606/130 |
| 2014/0142597 A1* | 5/2014 | Winkler | A61B 17/122 606/157 |
| 2016/0008001 A1* | 1/2016 | Winkler | A61B 17/122 606/157 |
| 2016/0151071 A1* | 6/2016 | Tokarz | A61B 17/1285 606/143 |
| 2016/0174981 A1* | 6/2016 | Fago | A61B 17/1227 606/157 |
| 2016/0249932 A1* | 9/2016 | Rogers | A61B 17/12013 606/144 |
| 2016/0296233 A1* | 10/2016 | Wheeler | A61B 17/0643 |
| 2016/0317154 A1* | 11/2016 | Kimura | A61B 8/0883 |
| 2016/0317155 A1* | 11/2016 | Kimura | A61B 17/12013 |
| 2017/0014135 A1* | 1/2017 | Martin | A61B 17/10 |
| 2017/0014137 A1* | 1/2017 | Martin | A61B 17/122 |
| 2017/0095257 A1* | 4/2017 | Miller | A61B 17/1227 |
| 2017/0135700 A1* | 5/2017 | Rogowski | A61B 17/1227 |
| 2017/0196568 A1* | 7/2017 | Gross | A61B 17/122 |
| 2017/0340335 A1* | 11/2017 | Ad | A61B 17/12013 |
| 2018/0036007 A1* | 2/2018 | Fago | A61B 17/122 |
| 2018/0199945 A1* | 7/2018 | Zhou | A61B 17/122 |

\* cited by examiner

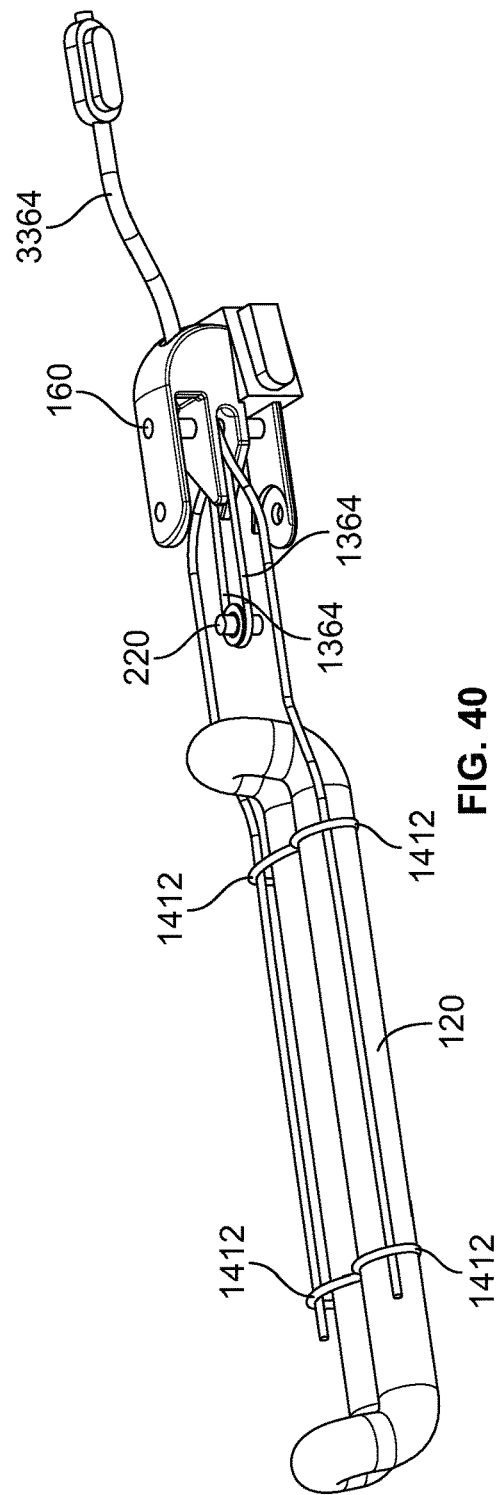

ROBOTIC ASSISTED CLIP APPLIER

INTRODUCTION TO THE INVENTION

The present disclosure is directed to medical instruments and, more specifically, to an applier that may be used to apply a left atrial appendage occlusion clip.

It is a first aspect of the present disclosure to provide a medical instrument comprising an end effector comprising a pair of repositionable jaws operatively coupled to an open-ended occlusion clip devoid of a handle control.

In a more detailed embodiment of the first aspect, the end effector includes a line concurrently mounted to the open-ended occlusion clip and the pair of repositionable jaws. In yet another more detailed embodiment, the line comprises at least a first line and a second line, the first line is concurrently mounted to the open-ended occlusion clip and a first of the pair of repositionable jaws, the second line is concurrently mounted to the open-ended occlusion clip and a second of the pair of repositionable jaws, and the first and second lines are repositionable to selectively dismount the first line from at least one of the open-ended occlusion clip and the first of the pair of repositionable jaws, and to selectively dismount the second line from at least one of the open-ended occlusion clip and the second of the pair of repositionable jaws. In a further detailed embodiment, the end effector includes pulleys operatively coupled to at least one of the pair of repositionable jaws. In still a further detailed embodiment, the first of the repositionable jaws is mounted to a first of the pulleys, the second of the repositionable jaws is mounted to a second of the pulleys, and a line engages the first and second pulleys. In a more detailed embodiment, the first repositionable jaw is mounted to a first and a third of the pulleys, the second repositionable jaw is mounted to a second and a fourth of the pulleys, and a line engages the first, second, third, and fourth pulleys. In a more detailed embodiment, each of the pair of repositionable jaws includes a channel configured to receive a deployment line, the deployment line operatively coupled to one of the pair of repositionable jaws and the open-ended occlusion clip. In another more detailed embodiment, the end effector includes at least one of a cavity and a projection configured to be engaged by a robotic grasper. In yet another more detailed embodiment, the end effector includes at least one of a plurality of projections and a plurality of cavities configured to be engaged by a robotic grasper. In still another more detailed embodiment, the open-ended occlusion clip comprises: (i) a first elongated occlusion arm; (ii) a second elongated occlusion arm; (iii) a first elongated biasing arm coupled to a distal portion of the first elongated occlusion arm; and, (iv) a second elongated biasing arm coupled to a distal portion of the second elongated occlusion arm, where a proximal portion of the first elongated biasing arm is coupled to a proximal portion of the second elongated biasing arm, where the first elongated occlusion arm extends parallel to the first elongated bias arm along a majority of its length, and where the second elongated occlusion arm extends parallel to the second elongated bias arm along a majority of its length.

It is a second aspect of the present invention to provide a medical instrument comprising an end effector comprising a first jaw configured to be repositionable with respect to a second jaw, the first and second jaws removably mounted to an open-ended occlusion clip, the end effector configured to be removably coupled to an open-ended occlusion clip with a pair of terminal ends and first and second robotic arms, and wherein the end effector includes at least one of a cavity and a projection configured to be engaged by at least one of the first and second robotic arms.

In a more detailed embodiment of the second aspect, the end effector further comprises at least a first line and a second line, the first line is concurrently mounted to the open-ended occlusion clip and the first jaw, the second line is concurrently mounted to the open-ended occlusion clip and the second jaw, and the first and second lines are selectively repositionable to dismount the first and second lines from the open-ended occlusion clip and the first and second jaws. In yet another more detailed embodiment, the end effector includes pulleys operatively coupled to the first and second jaws. In a further detailed embodiment, the first jaw is mounted to a first of the pulleys, the second jaw is mounted to a second of the pulleys, and a line engages the first and second pulleys. In still a further detailed embodiment, the open-ended occlusion clip comprises: (i) a first elongated occlusion arm; (ii) a second elongated occlusion arm; (iii) a first elongated biasing arm coupled to a distal portion of the first elongated occlusion arm; and, (iv) a second elongated biasing arm coupled to a distal portion of the second elongated occlusion arm, where a proximal portion of the first elongated biasing arm is coupled to a proximal portion of the second elongated biasing arm, where the first elongated occlusion arm extends parallel to the first elongated bias arm along a majority of its length, where the second elongated occlusion arm extends parallel to the second elongated bias arm along a majority of its length.

It is a third aspect of the present invention to provide a method of fabricating an end effector that includes a first jaw repositionable with respect to a second jaw, the first and second jaws removably coupled to an open-ended occlusion clip with dual terminal ends, the method comprising: (a) detachably mounting the open-ended occlusion clip to the first and second jaws using a first line; (b) threading at least one pulley mounted to each of the first and second jaws with a second line, where the line extends from a first pulley of the first jaw to a second pulley of the second jaw; and, (c) directing the first and second lines through a portion of the end effector.

In a more detailed embodiment of the third aspect, the act of threading at least one pulley includes threading multiple pulleys associated with each of the first and second jaws to create a double tackle configuration. In yet another more detailed embodiment, the act of detachably mounting the open-ended occlusion clip includes threading the first line through a plurality of loops extending through at least one of the first and second jaws, the plurality of loops being mounted to the open-ended occlusion clip.

It is a fourth aspect of the present invention to provide a necrosis clip and applier comprising: (a) an open-ended necrosis clip comprising a first beam longitudinally aligned with and spaced apart from a second beam, the first beam operatively coupled to and longitudinally aligned with a third beam, the second beam operatively coupled to and longitudinally aligned with a fourth beam, where the third and fourth beams are coupled to one another, and where the first and second beams each include an unattached terminal end; (b) an end effector including a first jaw and a second jaw repositionably mounted to a housing, the first and second jaws operatively coupled to at least a gun tackle pulley configuration utilized to reposition at least one of the first and second jaws with respect to one another, where the first and second jaws are detachably mounted to the open-ended necrosis clip; and, (c) a robotic coupling feature associated with the end effector and configured to be engaged by a robotic surgical instrument to removably couple the robotic surgical instrument to the end effector.

In a more detailed embodiment of the fourth aspect, the robotic coupling feature includes at least one of a cavity and a projection configured to be engaged by the robotic surgical instrument. In yet another more detailed embodiment, the end effector includes a first detachment line in operative engagement with the first jaw of the end effector and the necrosis clip, and the end effector includes a second detachment line in operative engagement with the second jaw of the end effector and the necrosis clip. In a further detailed embodiment, the first jaw and the second jaw each include a channel configured to receive at least one of the first detachment line and the second detachment line. In still a further detailed embodiment, the first detachment line extends through a first loop coupled to the first jaw when the open-ended necrosis clip is detachably mounted to the first jaw, the second detachment line extends through a second loop coupled to the second jaw when the open-ended necrosis clip is detachably mounted to the second jaw, the first detachment line does not extend through the first loop coupled to the first jaw when the open-ended necrosis clip is detached from to the first jaw, and the second detachment line does not extend through the second loop coupled to the second jaw when the open-ended necrosis clip is detached from to the second jaw. In a more detailed embodiment, the first jaw includes a first channel configured to receive the first detachment line, the first jaw includes a first orifice configured to receive the first loop, the second jaw includes a second channel configured to receive the second detachment line, and the second jaw includes a second orifice configured to receive the second loop. In a more detailed embodiment, at least the gun tackle pulley configuration includes a first pulley, a second pulley, and a third pulley, the first jaw is mounted to the first pulley and the third pulley, the second jaw is mounted to the second pulley, and the line is fixedly coupled to the second jaw and repositionably engages the first pulley, the second pulley, and the third pulley. In another more detailed embodiment, at least the gun tackle pulley configuration includes a first pulley, a second pulley, a third pulley, and a fourth pulley, the first jaw is mounted to the first pulley and the third pulley, the second jaw is mounted to the second pulley and the fourth pulley, and the line is fixedly coupled to the first jaw and repositionably engages the first pulley, the second pulley, the third pulley, and the fourth pulley. In yet another more detailed embodiment, the first jaw pivotally engages the second jaw.

It is a fifth aspect of the present invention to provide a method of deploying an occlusion clip comprising: (a) inserting an open-ended occlusion clip with dual terminal ends removably mounted to an end effector through at least one of an incision and a trocar, the end effector devoid of a handle control, the open-ended occlusion clip and the end effector operatively coupled to one another prior to insertion into and through at least one of the incision and the trocar; (b) repositioning the end effector using a first robotic tool to reposition the open-ended occlusion clip so the open-ended occlusion clip is interposed by a portion of a left atrial appendage between a base and a tip of the left atrial appendage without needing to pass a tip of the left atrial appendage between opposing clamping surfaces of the open-ended occlusion clip and without needing to pierce the left atrial appendage; (c) clamping the left atrial appendage with the open-ended occlusion clip to cause necrosis to the left atrial appendage by repositioning a second robotic tool with respect to the end effector; (d) discontinuing operative coupling between the open-ended occlusion clip and the end effector; and, (e) withdrawing the end effector through at least one of the incision and the trocar.

In a more detailed embodiment of the fifth aspect, the inserting step occurs during at least one of an open sternotomy, a left thoracotomy, a right thoracotomy, a left port procedure, a right port procedure, a subxiphoid approach, and a transdiaphragmatic approach. In yet another more detailed embodiment, the method further includes insufflating a thoracic space prior to the inserting step. In a further detailed embodiment, the method further includes making an incision as part of a procedure comprising at least one of an open sternotomy, a left thoracotomy, a right thoracotomy, a left port procedure, a right port procedure, a subxiphoid approach, and a transdiaphragmatic approach, in addition to introducing a trocar through the incision. In still a further detailed embodiment, a first line is operatively coupled the end effector. In a more detailed embodiment, the end effector includes a first jaw operatively coupled to the open-ended occlusion clip, the end effector includes a second jaw operatively coupled to the open-ended occlusion clip, and repositioning the end effector to reposition the open-ended occlusion clip includes tensioning the first line to cause increased spacing between the first jaw and the second jaw. In a more detailed embodiment, the method further includes grasping the left atrial appendage concurrent with repositioning the end effector deployment device to reposition the occlusion clip so the open end of the open-ended occlusion clip is interposed by the portion of the left atrial appendage. In another more detailed embodiment, the method further includes repeating the repositioning and clamping steps prior to the disengaging step. In yet another more detailed embodiment, the method further includes confirming a clamping position of the open-ended occlusion clip is operative to cause necrosis to the left atrial appendage using at least one of visualization and a transesophageal echocardiogram. In still another more detailed embodiment, the inserting step includes inserting the open-ended occlusion clip and the end effector through the trocar, the withdrawing step includes withdrawing the end effector through the trocar, and the trocar comprises a twelve millimeter or less diameter cross-section.

It is a sixth aspect of the present invention to provide a method of deploying a necrosis clip comprising: (a) inserting an open-ended necrosis clip having dual terminal ends through a trocar, the open-ended necrosis clip removably mounted to an end effector at least partially including at least a gun tackle pulley configuration; (b) repositioning the end effector using a robotic arm to spatially reposition the open-ended necrosis clip proximate a portion of a left atrial appendage; (c) opening the open-ended necrosis clip using at least the gun tackle pulley configuration of the end effector to allow an open end of the open-ended necrosis clip to be interposed by a portion of a left atrial appendage, the portion of the left atrial appendage being between a base and a tip of the left atrial appendage, without passing the tip of the left atrial appendage between opposing clamping surfaces of the open-ended necrosis clip; (d) repositioning the end effector using the first robotic tool so the portion of the left atrial appendage interposes the opposing clamping surfaces of the open-ended necrosis clip; (e) clamping the left atrial appendage in an initial position between the opposing clamping surfaces of the open-ended necrosis clip by repositioning a second robotic tool; (f) assessing the operability of the open-ended necrosis clip in the initial position to cause necrosis of the left atrial appendage; and, (g) repositioning the open-ended necrosis clip to a subsequent position, different from the initial position, where the left atrial appendage is clamped between the opposing clamping surfaces of the open-ended necrosis clip, where repositioning the open-ended necrosis clip from the initial position to the subsequent position is repeatable without affecting the structural integrity of the left atrial appendage.

In a more detailed embodiment of the sixth aspect, the method further includes disengaging the open-ended necrosis clip from the end effector post initiation of necrosis of the left atrial appendage tip, and withdrawing the end effector through at least one of the incision and the trocar post disengaging the open-ended necrosis clip from the end effector. In yet another more detailed embodiment, the inserting step occurs during at least one of an open sternotomy, a left thoracotomy, a right thoracotomy, a left port procedure, a right port procedure, a subxiphoid approach, and a transdiaphragmatic approach. In a further detailed embodiment, the method further includes insufflating a thoracic space prior to the inserting step. In still a further detailed embodiment, the method further includes making an incision as part of a procedure comprising at least one of an open sternotomy, a left thoracotomy, a right thoracotomy, a left port procedure, a right port procedure, a subxiphoid approach, and a transdiaphragmatic approach, and introducing a trocar through the incision. In a more detailed embodiment, the method further includes grasping the left atrial appendage concurrent with repositioning the end effector deployment device to reposition the necrosis clip so the open end of the open-ended necrosis clip is interposed by the portion of the left atrial appendage. In a more detailed embodiment, the method further includes confirming application of the full bias of the open-ended necrosis clip is operative to cause necrosis of the left atrial appendage using at least one of visualization and a transesophageal echocardiogram. In another more detailed embodiment, the method further includes disengaging the open-ended necrosis clip from the end effector, wherein disengaging the open-ended necrosis clip from the end effector includes disengaging at least one wire operatively coupled to end effector and the open-ended necrosis clip. In yet another more detailed embodiment, the inserting step includes inserting the open-ended necrosis clip and the end effector through the trocar, and the trocar comprises a twelve millimeter or less diameter orifice.

It is a seventh aspect of the present invention to provide a necrosis clip and applier comprising: (a) an open-ended necrosis clip comprising a first beam longitudinally aligned with and spaced apart from a second beam, the first beam operatively coupled to and longitudinally aligned with a third beam, the second beam operatively coupled to and longitudinally aligned with a fourth beam, where the third and fourth beams are coupled to one another, and where the first and second beams each include an unattached terminal end; (b) an end effector including a first jaw and a second jaw repositionably mounted to a housing, where the first and second jaws are detachably mounted to the open-ended necrosis clip, the end effector also including a mechanical including component parts that are configured to allow rotational and angular repositioning with respect to a longitudinal axis extending through the mechanical joint.

In a more detailed embodiment of the seventh aspect, the mechanical joint includes a ball and socket joint. In yet another more detailed embodiment, the end effector includes at least one of a cavity and a projection configured to be engaged by a robotic grasper. In a further detailed embodiment, the first and second jaws are operatively coupled to at least a gun tackle pulley configuration utilized to reposition at least one of the first and second jaws with respect to one another, wherein the end effector further includes a line in communication with at least the gun tackle pulley configuration, and wherein the line extends beyond the bounds of the end effector. In still a further detailed embodiment, the apparatus further includes a first connector in operative engagement with at least one of the open-ended necrosis clip and the end effector. In a more detailed embodiment, the first connector includes a first detachment line in operative engagement with the first jaw of the end effector and the open-ended necrosis clip, and the first connector includes a second detachment line in operative engagement with the second jaw of the end effector and the open-ended necrosis clip. In a more detailed embodiment, the first jaw and the second jaw each include a channel configured to receive at least one of the first detachment line and the second detachment line. In another more detailed embodiment, the first detachment line extends through a first loop coupled to the first jaw when the open-ended necrosis clip is detachably mounted to the first jaw, the second detachment line extends through a second loop coupled to the second jaw when the open-ended necrosis clip is detachably mounted to the second jaw, the first detachment line does not extend through the first loop coupled to the first jaw when the open-ended necrosis clip is detached from to the first jaw, and the second detachment line does not extend through the second loop coupled to the second jaw when the open-ended necrosis clip is detached from to the second jaw. In yet another more detailed embodiment, the first jaw includes a first channel configured to receive the first detachment line, the first jaw includes a first orifice configured to receive the first loop, the second jaw includes a second channel configured to receive the second detachment line, and the second jaw includes a second orifice configured to receive the second loop. In still another more detailed embodiment, at least the gun tackle pulley configuration includes a first pulley, a second pulley, and a third pulley, the first jaw is mounted to the first pulley and the third pulley, the second jaw is mounted to the second pulley, and the line is fixedly coupled to the second jaw and repositionably engages the first pulley, the second pulley, and the third pulley.

In yet another more detailed embodiment of the seventh aspect, at least the gun tackle pulley configuration includes a first pulley, a second pulley, a third pulley, and a fourth pulley, the first jaw is mounted to the first pulley and the third pulley, the second jaw is mounted to the second pulley and the fourth pulley, and the line is fixedly coupled to the first jaw and repositionably engages the first pulley, the second pulley, the third pulley, and the fourth pulley. In yet another more detailed embodiment, first jaw pivotally engages the second jaw. In a further detailed embodiment, the end effector includes a pair of projections configured to be grasped by a robotic fenestrated grasper.

It is an eighth aspect of the present invention to provide a medical instrument comprising: (a) a pair of repositionable jaws; (b) an occlusion clip detachably mounted to the pair of repositionable jaws; (c) a folding support concurrently mounted to the pair of repositionable jaws, the folding support repositionable between a folded position and an unfolded position, where the folded position has the pair of repositionable jaws in closer proximity to one another than in the unfolded position, and a first connection operatively coupled to the folding support and configured to be repositioned by an instrument otherwise untethered from the folding support, the first connection repositionable with respect to the folding support to facilitate repositioning of the folding support between the folded position and the unfolded position.

In a more detailed embodiment of the eighth aspect, the apparatus further comprises a second connection operatively coupled to the occlusion clip and at least one of the pair of repositionable jaws when the occlusion clip is mounted to the pair of repositionable jaws, the second connection being configured to be repositioned and discontinue operative coupling between at least one of the occlusion clip and at least one of the pair of repositionable jaws. In yet another more detailed embodiment, the second connection comprises a line. In a further detailed embodiment, the line includes a first wire and a second wire, the first wire is concurrently mounted to the occlusion clip and a first of the pair of repositionable jaws, the second wire is concurrently mounted to the occlusion clip and a second of the pair of repositionable jaws, the line is repositionable to selectively dismount the first wire from at least one of the occlusion clip and the first of the pair of repositionable jaws, and is repositionable to selectively dismount the second wire from at least one of the occlusion clip and the second of the pair of repositionable jaws. In still a further detailed embodiment, the line includes a first wire, the first wire is concurrently mounted to the occlusion clip and a first of the pair of repositionable jaws at a first location, and concurrently mounted to the occlusion clip and a second of the pair of repositionable jaws at a second location, the line is repositionable to selectively dismount the occlusion clip and the first of the pair of repositionable jaws, as well as repositionable to selectively dismount the occlusion clip and the second of the pair of repositionable jaws. In a more detailed embodiment, the folding support is operatively coupled to a pulley and the first link. In a more detailed embodiment, the folding support includes: (i) a first link concurrently repositionably and operatively coupled to a first of the pair of repositionable jaws; (ii) a second link concurrently repositionably and operatively coupled to a second of the pair of repositionable jaws; (iii) a third link concurrently repositionably and operatively coupled to the first of the pair of repositionable jaws and the second link; and, (iv) a fourth link concurrently repositionably and operatively coupled to the second of the pair of repositionable jaws and the first link, where the third link is repositionably and operatively coupled to the fourth link. In another more detailed embodiment, the folding support includes a fifth link concurrently repositionably and operatively coupled to a sixth link and to the first link, wherein the sixth link is concurrently repositionably and operatively coupled to the fifth link and to the second link. In yet another more detailed embodiment, the fifth and sixth links are both mounted to and repositionable with respect to a pulley. In still another more detailed embodiment, the second joint includes a first camming surface to facilitate repositioning of the fifth link, and the second joint includes a second camming surface to facilitate repositioning of the sixth link.

In yet another more detailed embodiment of the eighth aspect, the first connection is operatively coupled to the fifth and sixth links. In yet another more detailed embodiment, the first connection includes a pulley operatively coupled to the fifth and sixth links. In a further detailed embodiment, the folding support comprises a folding pantograph support.

It is a ninth aspect of the present invention to provide a method of deploying an occlusion clip comprising: (a) inserting an occlusion clip removably mounted to an end effector deployment device having repositionable jaws through at least one of an incision and a trocar, the occlusion clip and the end effector deployment device mounted to one another when inserted into and through at least one of the incision and the trocar, the end effector deployment device including a folding support concurrently mounted to the pair of repositionable jaws, the end effector deployment device also including at least one of a projection and a cavity configured to be engaged by a first surgical otherwise untethered to the end effector deployment device; (b) repositioning the end effector proximate a left atrial appendage by using a second surgical device; (c) repositioning the folding support by using a second surgical device, which is otherwise untethered from the end effector deployment device, to reposition the occlusion clip so the occlusion clip is interposed by a part of a left atrial appendage in between a base and a tip of the left atrial appendage by passing the tip of the left atrial appendage between opposing clamping surfaces of the occlusion clip; (d) repositioning the folding support by using the second surgical device in order for the occlusion clip to clamp the left atrial appendage and occlude a portion of the left atrial appendage without piercing the left atrial appendage; (e) disengaging the occlusion clip from the end effector deployment device; and, (f) withdrawing the end effector deployment device through at least one of the incision and the trocar.

In a more detailed embodiment of the ninth aspect, the inserting step occurs during at least one of an open sternotomy, a left thoracotomy, a right thoracotomy, a left port procedure, a right port procedure, a subxiphoid approach, and a transdiaphragmatic approach. In yet another more detailed embodiment, the method further includes insufflating a thoracic space prior to the inserting step. In a further detailed embodiment, the method further includes making an incision as part of a procedure comprising at least one of an open sternotomy, a left thoracotomy, a right thoracotomy, a left port procedure, a right port procedure, a subxiphoid approach, and a transdiaphragmatic approach, and introducing a trocar through the incision. In still a further detailed embodiment, the method further includes grasping the left atrial appendage concurrent with repositioning the end effector deployment device to reposition the occlusion clip so the occlusion clip is interposed by the portion of the left atrial appendage. In a more detailed embodiment, the method further includes repeating the repositioning and clamping steps prior to the disengaging step. In a more detailed embodiment, the method further comprising confirming a clamping position of the occlusion clip is operative to occlude the portion of the left atrial appendage using at least one of visualization and a transesophageal echocardiogram. In another more detailed embodiment, the inserting step includes inserting the occlusion clip and the end effector deployment device through the trocar, the withdrawing step includes withdrawing the end effector deployment device through the trocar, and the trocar comprises a twelve millimeter or less diameter orifice It is a tenth aspect of the present invention to provide a method of deploying an occlusion clip comprising: (a) inserting an occlusion clip removably mounted to an end effector deployment device having repositionable jaws through at least one of an incision and a trocar, the occlusion clip and the end effector deployment device mounted to one another when inserted into and through at least one of the incision and the trocar, the end effector deployment device including a folding support concurrently mounted to the pair of repositionable jaws; (b) repositioning the end effector deployment device to reposition the occlusion clip so the occlusion clip is interposed by a portion of a left atrial appendage interposing a base and a tip of the left atrial appendage by passing the tip of the left atrial appendage between opposing clamping surfaces of the occlusion clip; (c) clamping the left atrial appendage with the occlusion clip in an initial position without piercing the left atrial appendage between the occlusion clip; (d) assessing the operability of the occlusion clip in the initial position to occlude the left atrial appendage; and, (e) repositioning the end effector deployment device to reposition the occlusion clip to a subsequent position, different from the initial position, to clamp the left atrial appendage, where repositioning the occlusion clip from the initial position to the subsequent position is repeatable without affecting the structural integrity of the left atrial appendage.

It is an eleventh aspect of the present invention to provide a method of deploying an occlusion clip comprising: (a) inserting an occlusion clip removably mounted to an end effector deployment device, including repositionable jaws and a folding support concurrently mounted to the repositionable jaws, through at least one of an incision and a trocar, the occlusion clip biased to a clamping position; (b) repositioning the end effector deployment device to counteract a bias of the occlusion clip and reposition the occlusion clip to a tissue insertion position where the full bias of the occlusion clip is not applied to a left atrial appendage tissue; (c) repositioning the end effector deployment device to reposition the occlusion clip in the tissue insertion position so a portion of a left atrial appendage between a base and a tip of the left atrial appendage interposes the occlusion clip by having the tip of the left atrial appendage pass between opposing beams of the occlusion clip; (d) repositioning the occlusion clip to apply the full bias to the left atrial appendage; and (e) removing the end effector deployment device from around the left atrial appendage without passing the tip of the left atrial appendage between the repositionable jaws.

In a more detailed embodiment of the eleventh aspect, the method further includes disengaging the occlusion clip from the end effector deployment device, and withdrawing the end effector deployment device through at least one of the incision and the trocar. In yet another more detailed embodiment, the inserting step occurs during at least one of an open sternotomy, a left thoracotomy, a right thoracotomy, a left port procedure, a right port procedure, a subxiphoid approach, and a transdiaphragmatic approach. In a further detailed embodiment, the method further includes insufflating a thoracic space prior to the inserting step. In still a further detailed embodiment, the method further includes making an incision as part of a procedure comprising at least one of an open sternotomy, a left thoracotomy, a right thoracotomy, a left port procedure, a right port procedure, a subxiphoid approach, and a transdiaphragmatic approach, and introducing a trocar through the incision. In a more detailed embodiment, the method further includes grasping the left atrial appendage concurrent with repositioning the end effector deployment device to reposition the occlusion clip so the open end of the occlusion clip is interposed by the portion of the left atrial appendage. In a more detailed embodiment, the method further includes confirming application of the full bias of the occlusion clip is operative to occlude the left atrial appendage using at least one of visualization and a transesophageal echocardiogram. In another more detailed embodiment, the inserting step includes inserting the occlusion clip and the end effector deployment device through the trocar, and the trocar comprises a twelve millimeter or less diameter orifice. In yet another more detailed embodiment, the repositionable jaws include a pair of jaws that at least one of parallel open and parallel close, the pair of jaws comprise a first jaw and a second jaw, the first jaw is pivotally mounted to a first drive link and a first parallel link, the second jaw is pivotally mounted to a second drive link and a second parallel link, at least two of the first drive link, the second drive link, the first parallel link, and the second parallel link are pivotally mounted to a pulley.

BRIEF DESCRIPTION OF THE DRAWINGS

FIG. 40 is an elevated perspective view of the exemplary end effector and occlusion clip of FIG. 37 shown without repositionable jaws, first and second drive links, first and second parallel links, and first and second toggles.

DETAILED DESCRIPTION

The exemplary embodiments of the present disclosure are described and illustrated below to encompass devices, methods, and techniques relating to surgical procedures. Of course, it will be apparent to those of ordinary skill in the art that the embodiments discussed below are exemplary in nature and may be reconfigured without departing from the scope and spirit of the present disclosure. It is also to be understood that variations of the exemplary embodiments contemplated by one of ordinary skill in the art shall concurrently comprise part of the instant disclosure. However, for clarity and precision, the exemplary embodiments as discussed below may include optional steps, methods, and features that one of ordinary skill should recognize as not being a requisite to fall within the scope of the present disclosure.

Figure 1:
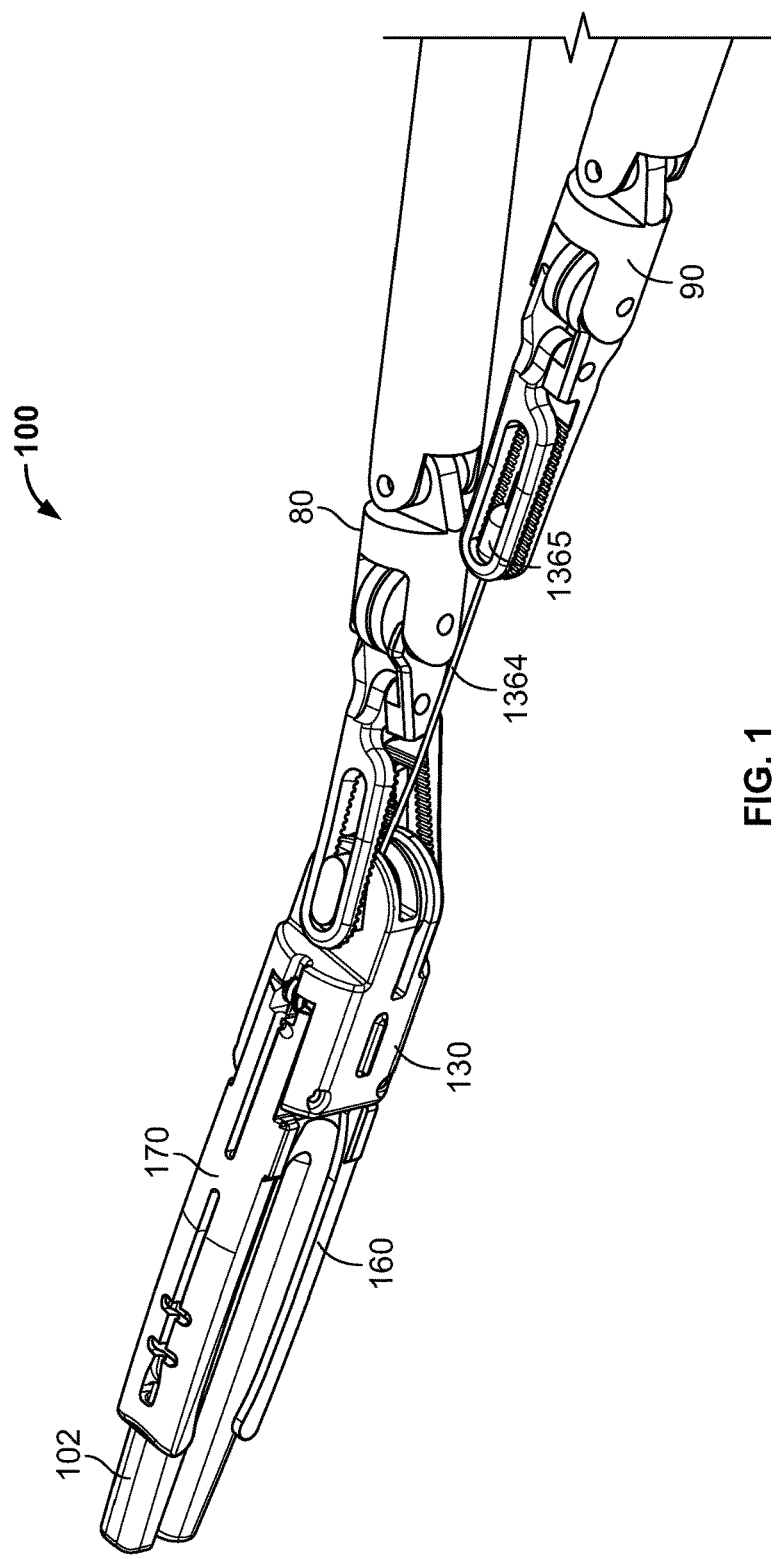
FIG. 1 is an elevated perspective view of a first exemplary end effector coupled to a clip in a closed position in accordance with the instant disclosure shown coupled to first and second robotic graspers.
Figure 2:
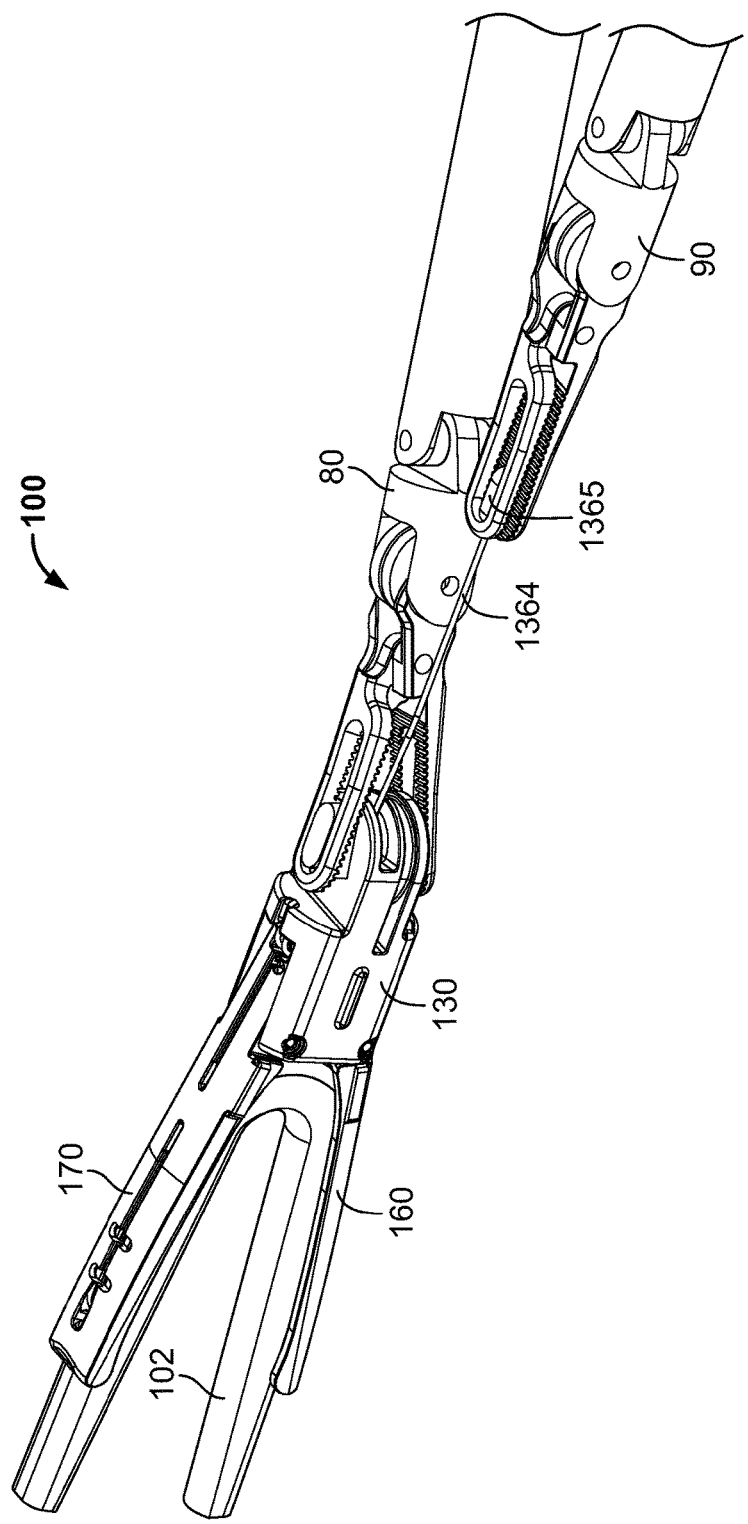
FIG. 2 is an elevated perspective view of the first exemplary end effector of FIG. 1, while coupled to a clip, shown with the clip in an open position in accordance with the instant disclosure when coupled to first and second robotic graspers.
Figure 3:
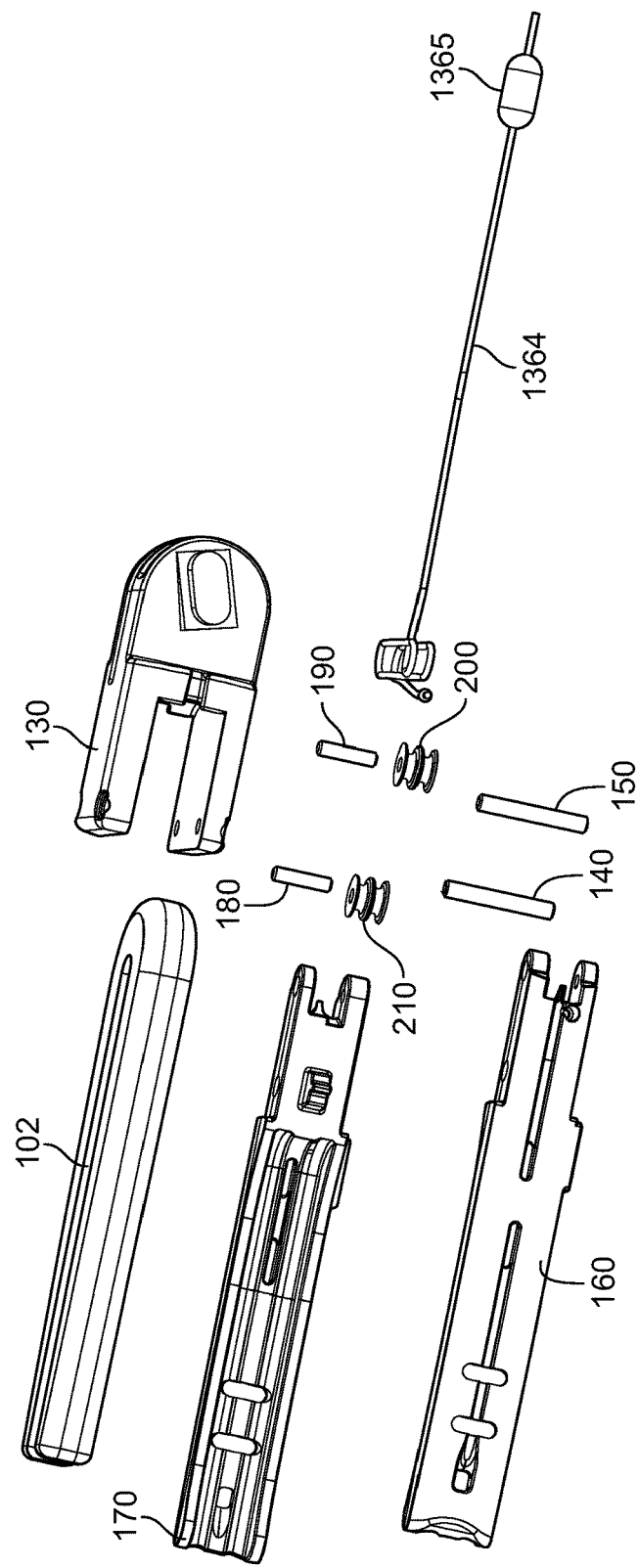
FIG. 3 is an exploded view of the first exemplary end effector of FIG. 1 with the occlusion clip.
Figure 4:
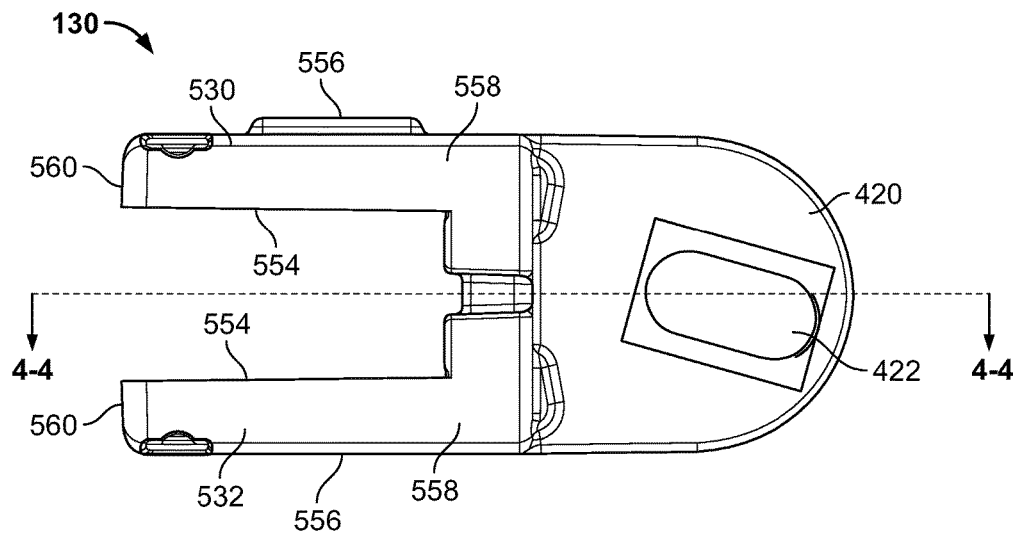
FIG. 4 is a top view of an exemplary housing comprising part of the first exemplary end effector of FIG. 1.
Figure 5:
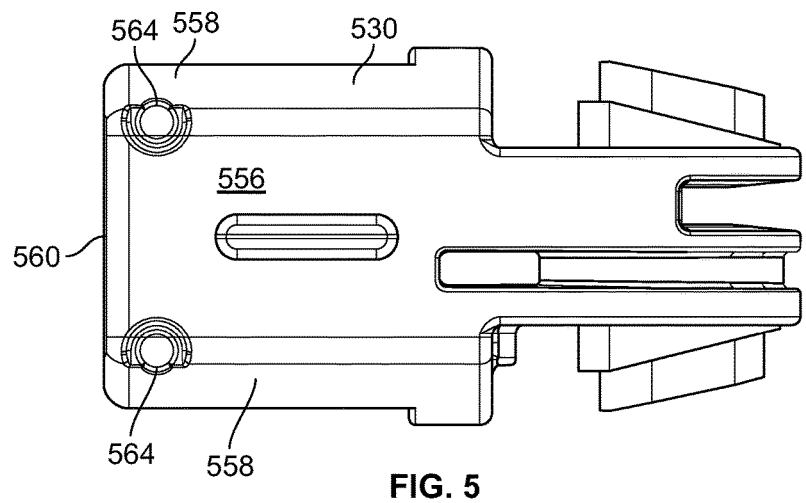
FIG. 5 is a profile view of the exemplary housing of FIG. 4.
Figure 6:
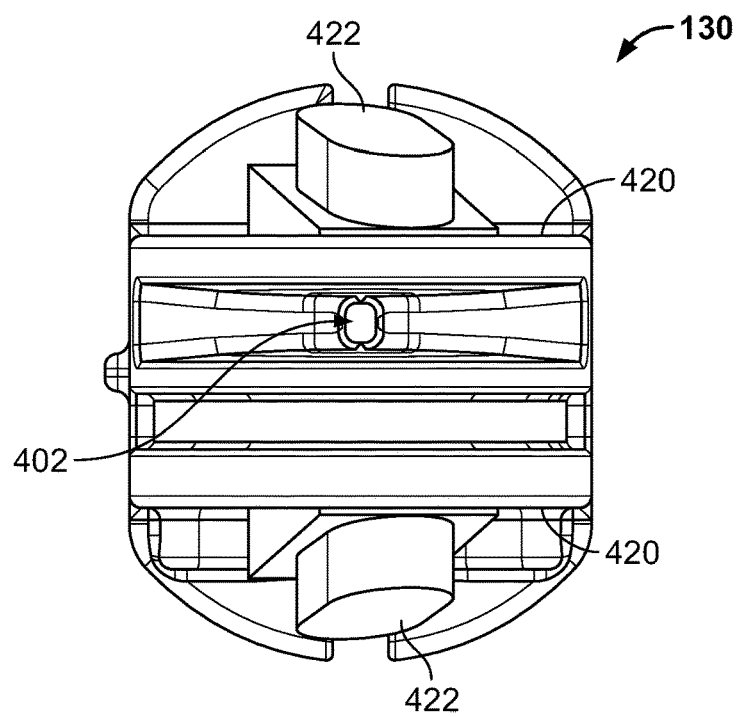
FIG. 6 is a proximal end view of the exemplary housing of FIG. 4.
Figure 7:
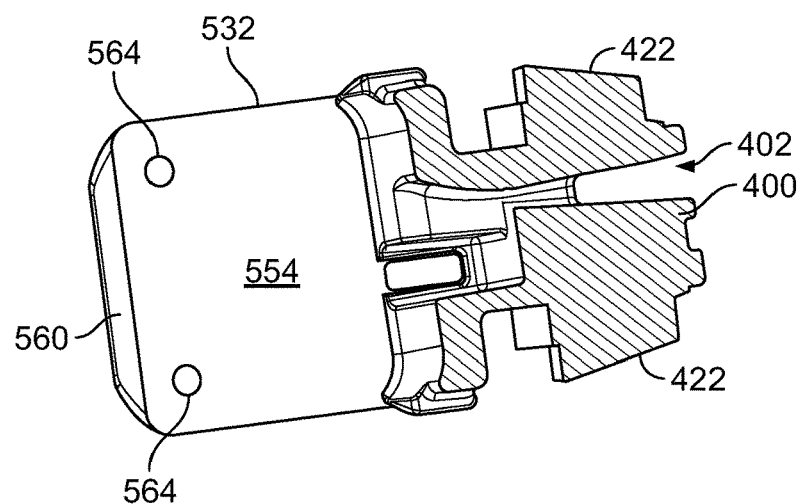
FIG. 7 is a cross-sectional view of the exemplary housing of FIG. 4 taken along line 4-4.
Figure 8:
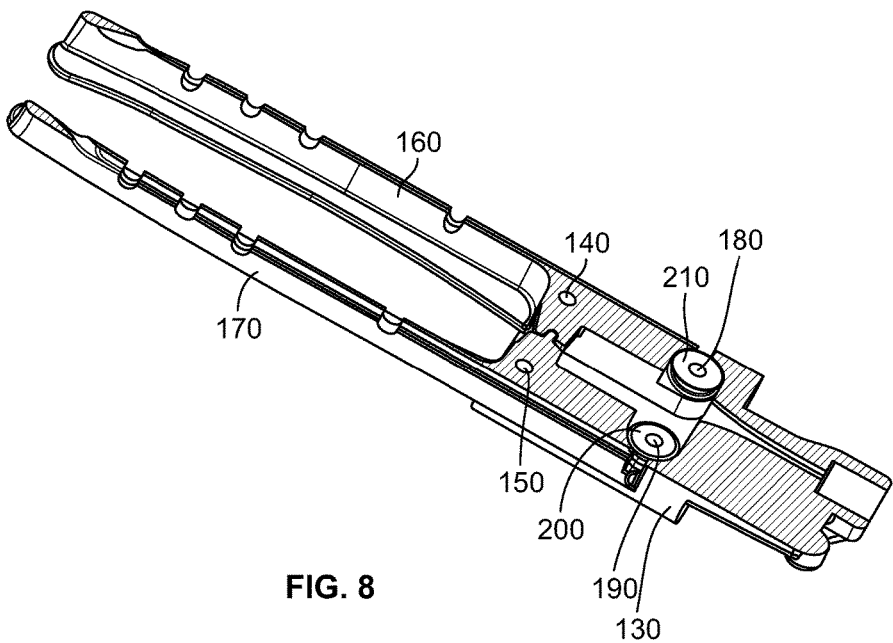
FIG. 8 is a cross-sectional view of portions of the exemplary end effector of FIG. 9 taken along line 9-9.
Figure 9:
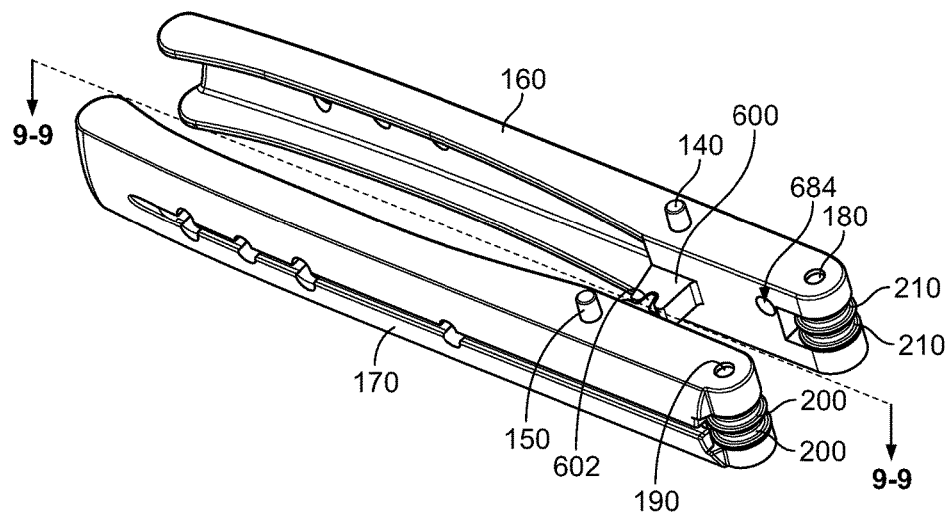
FIG. 9 is an elevated perspective view of portions of the exemplary end effector in a closed position.

Referencing FIGS. 1-3, a first exemplary robotic end effector 100 may be used in minimally invasive surgical procedures to allow deployment of an LAA occlusion clip 102 with respect to a left atrial appendage (not shown) with the assistance of a surgical position, such as a robotic arm having a robotic grasper 104 provided as part of the da Vinci surgical system available from Intuitive Surgical. U.S. Provisional Patent Application No. 62/091,230, and U.S. Non-provisisonal patent application Ser. No. 14/964,930, which each describe an exemplary LAA occlusion/necrosis clip 102, are incorporated herein by reference. As will be apparent to those skilled in the art after reviewing the instant disclosure, the end effector 100 may be utilized in capacities other than LAA occlusion clip deployment, each of which is within the scope of this disclosure.

Figure 10:
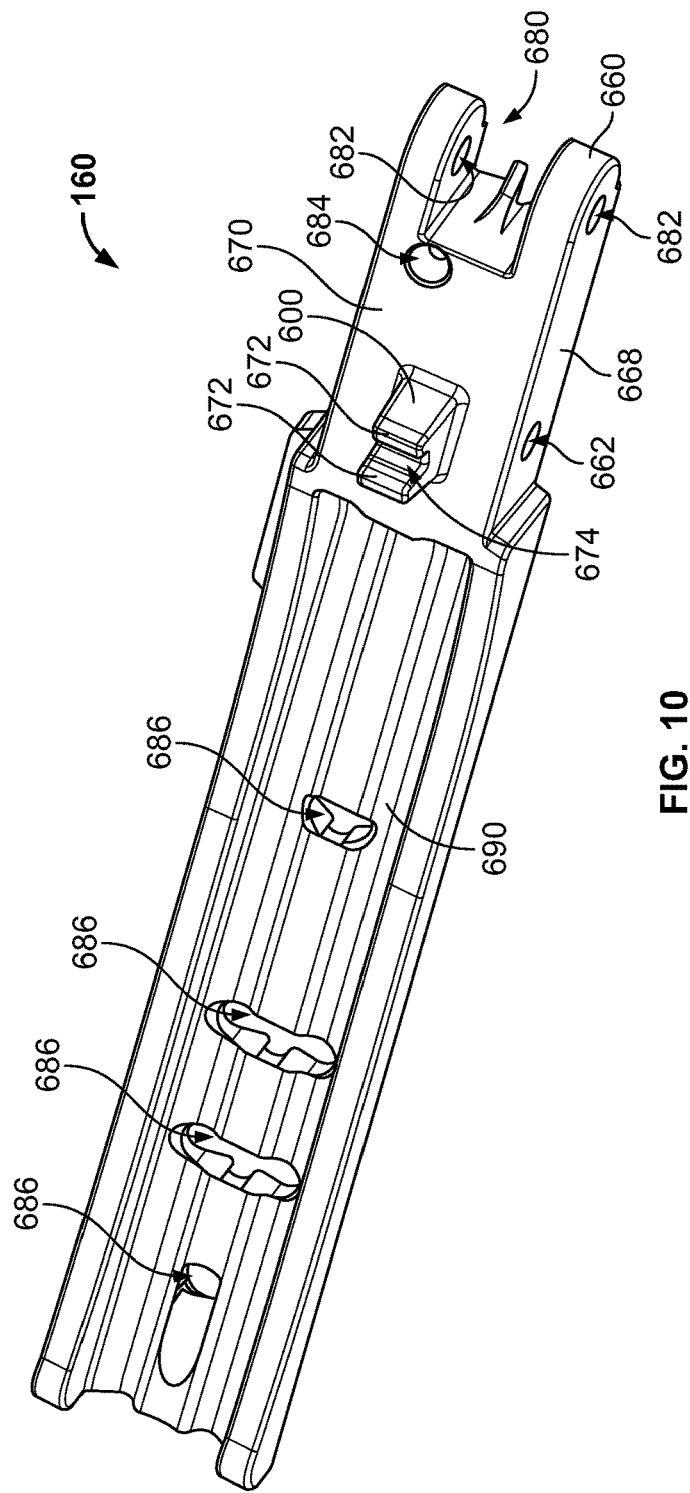
FIG. 10 is an elevated perspective view from an interior, proximal end of a first jaw in accordance with the instant invention.
Figure 11:
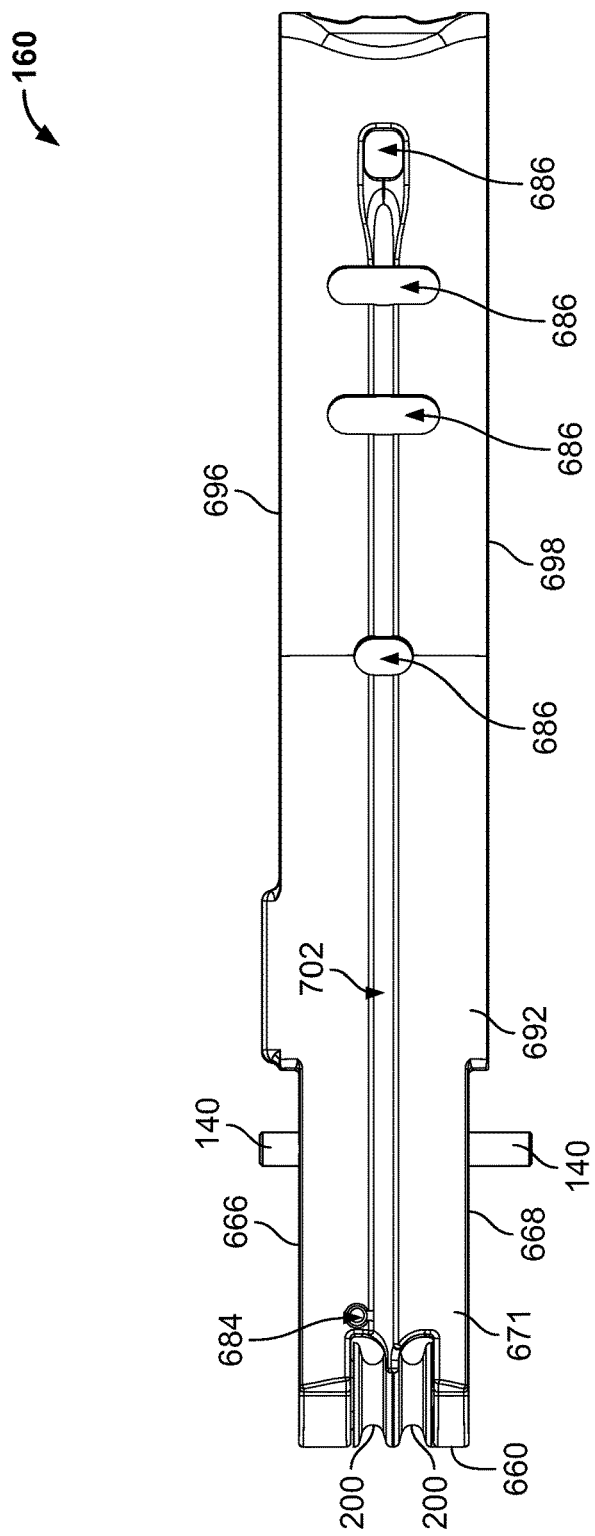
FIG. 11 is an exterior side view of the first jaw of FIG. 10.
Figure 12:
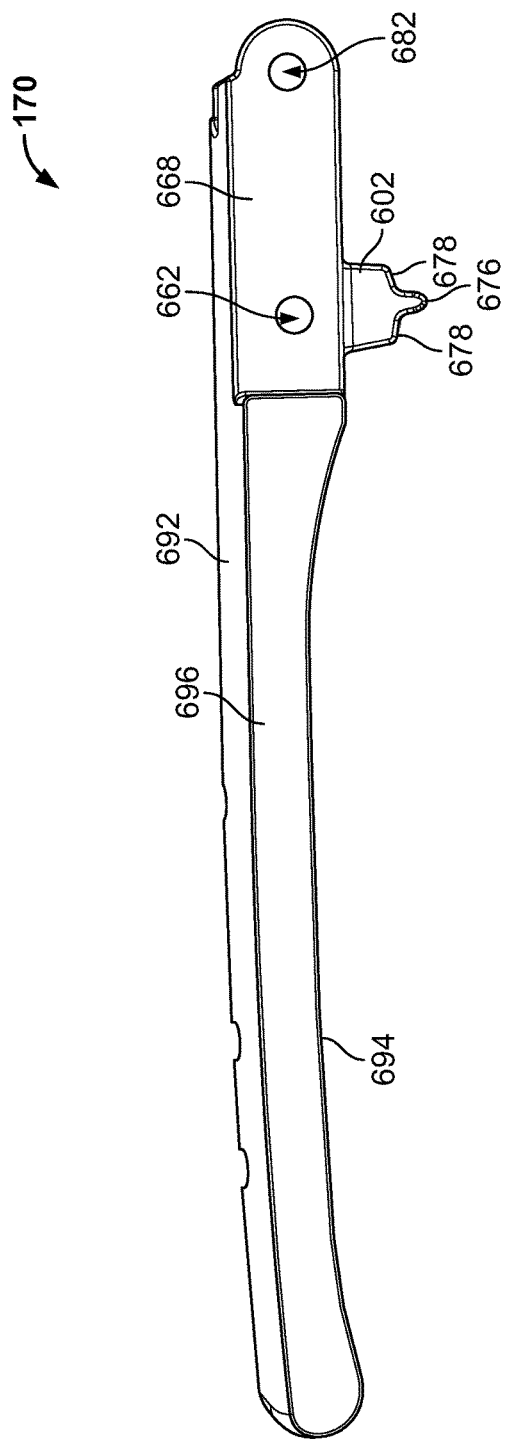
FIG. 12 is a bottom view of a second jaw in accordance with the instant disclosure.
Figure 13:
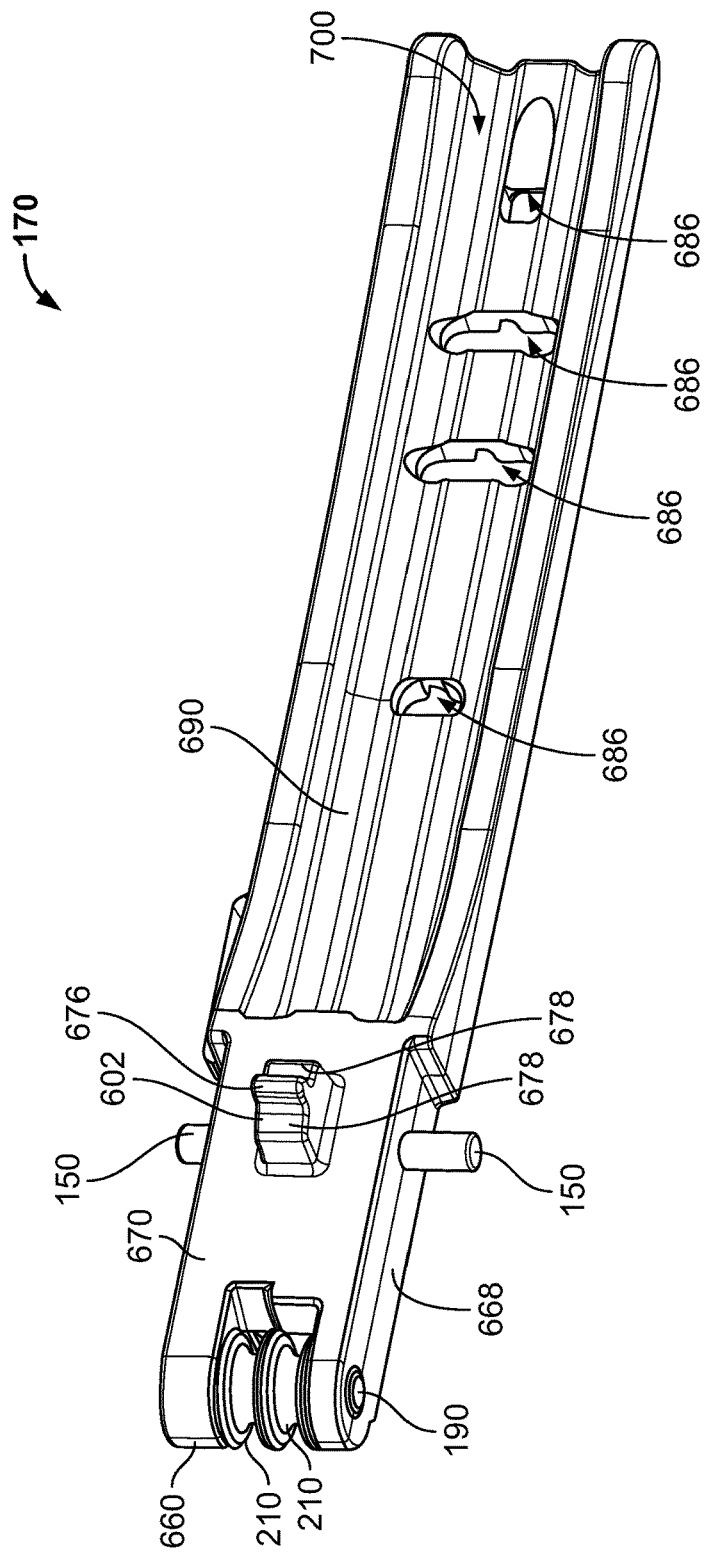
FIG. 13 is an elevated perspective view from an interior, proximal end of the second jaw of FIG. 12.

The end effector 100 comprises a housing 130 that is mounted distally to a first pin 140 and a second pin 150 that extend through corresponding distal openings 662 of a first jaw 160 and a second jaw 170 (see FIG. 10). In this fashion, the jaws 160, 170 are rotatably repositionable with respect to the housing 130 and with respect to one another. Each jaw 160, 170 includes a set of U-shaped proximal projections that overlap one another and each include a through opening 682 aligned with one another configured to receive a respective third pin 180 and fourth pin 190 (see FIG. 10). The spacing between the U-shaped projections is sufficient to each accommodate a respective pair of pulleys 200, 210 that rotate about a respective pin 180, 190. As will be discussed in more detail hereafter, a control wire 1364 is fed around the pulleys 200, 210 and is utilized to cause the jaws 160, 170 to pivot with respect to one another and with respect to the housing 130 for opening and closing in a non-parallel fashion. More specifically, when a first fenestrated robotic grasper 80 sandwiches the housing 130, and a second fenestrated robotic grasper 90 captures an enlarged portion 1365 of the control wire 1364, continued tensioning of the control wire resulting from movement of the second fenestrated robotic grasper away from the housing 130 causes the first and second jaws 160, 170 to pivot with respect to one another and cause the occlusion/necrosis clip 102 mounted thereto to progressively open. FIG. 1 depicts the occlusion/necrosis clip 102 in a closed position, while FIG. 2 depicts the occlusion/necrosis clip 102 in an open position. A more detailed discussion of the component parts of the end effector 100 follows.

Figure 14:
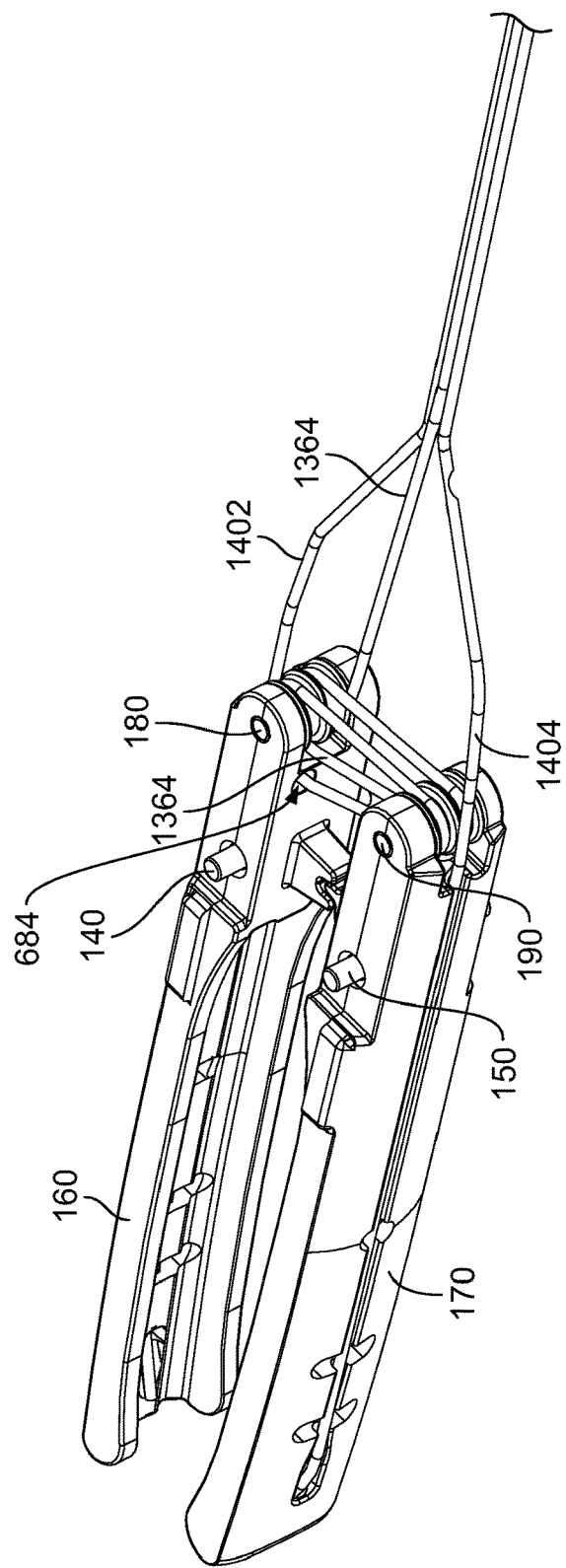
FIG. 14 is an elevated perspective view from a proximal end, taken of a portion of the first exemplary end effector without the exemplary housing to show orientation and positioning of deployment wires and control wires for the exemplary jaws in accordance with the instant disclosure.
Figure 15:
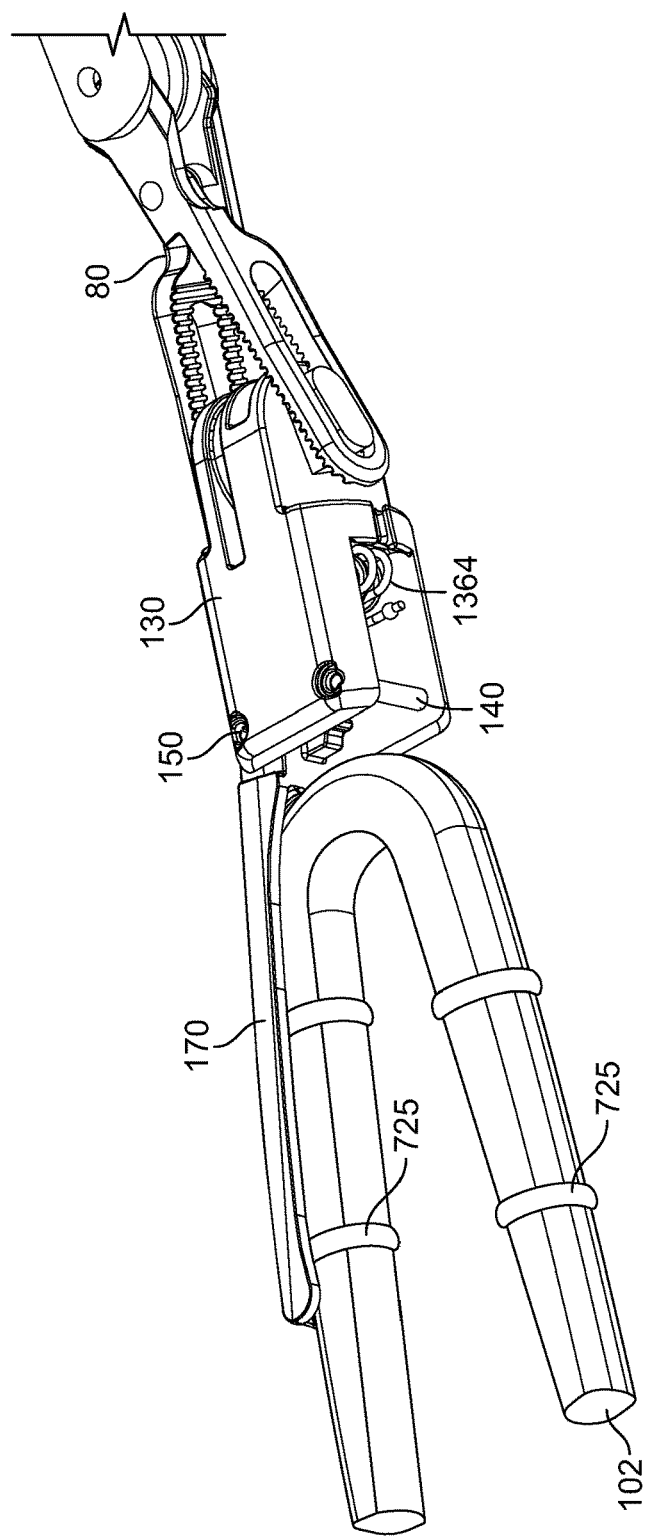
FIG. 15 is an elevated perspective view of the end effector of FIG. 1 shown partially mounted to an occlusion clip via one jaw, while the second jaw is not shown to depict the position of the suture loops with respect to the clip when otherwise mounted to the dual jaws when the jaws are in an open position.

As shown in FIGS. 4-7, the housing 130 includes an outer shell 400 that defines a longitudinal passage 402 extending therethrough. The longitudinal passage 402 is sized to accommodate the control wire 1364 coupled to the pulleys 200, 210 (see FIG. 3) in addition to a pair of deployment wires 1402, 1404 (see FIG. 14) used to selectively couple the occlusion clip 102 to the respective jaws 160, 170. As will be discussed in more detail hereafter, repositioning of the control wire 1364 with respect to the housing 130 and pulleys 200, 210 results in component motion operative to increase or decrease the distance between the distal ends of the opposing jaws 160, 170 (when the occlusion clip 102 is mounted to the jaws 160, 170, this component motion is also operative to open or close the occlusion clip).

The outer shell 400 also includes a ledge 420 on its proximal end from which extend opposing projections 422. The projections 422 are sized to allow grasping by the first fenestrated robotic grasper 80, such as a robotic grasper provided as part of the da Vinci surgical system available from Intuitive Surgical. As will be discussed in more detail hereafter, first fenestrated robotic grasper 80 is intended to direct repositioning of the end effector 100 independent of the position of the second fenestrated robotic grasper 90.

Opposite the proximal end, the outer shell 400 is configured to be repositionably mounted to the jaws 160, 170 on its distal end.

In exemplary form, a distal end of the housing 130 includes a pair of outer retention arms 530, 532 each including facing interior planar surfaces 554, that are bridged laterally by complementary arcuate surfaces 558 and opposing exterior surfaces 556. A distal most portion of each retention arm 530, 532 includes a planar surface 560 normal to the interior and exterior surfaces 554, 556. In this exemplary embodiment, the retention arms 530, 532 have a rounded, rectangular footprint typified by the interior surfaces 554 having a rounded rectangular footprint slightly larger than the exterior surfaces 556 rounded rectangular footprint. Proximate the distal, ninety degree corners of the retention arms 530, 532 are corresponding through holes 564 that extend between the interior and exterior surfaces 554, 556.

Each through hole 564 is sized to receive at least one of the first pin 140 and the second pin 150 in order to pivotally mount a corresponding jaw 160, 170 to the housing 130 (see FIG. 3). In this exemplary embodiment, each through hole 564 is sized to retain a corresponding pin 140, 150 therein via a friction fit (though fits other than a friction fit may be utilized) so that the pin does not rotate with respect to the housing 130, but nonetheless the jaws 160, 170 are able to rotate about the pins 140, 50. It should be noted that alternatively, for example, the through holes 564 may be sized to allow rotation of a corresponding pin 140, 150 therein so that the pins and jaws 160, 170 rotate together with respect to the housing 130 (in which case the pin 140, 150 received by a respective jaw 160, 170 may not be independently rotationally repositionable with respect to that jaw).

Referencing FIGS. 8-14, the jaws 160, 170 are structurally mirror images of one another, with the exception of the cams 600, 602. Consequently, the following discussion of the structure of a jaw is generally applicable to both the first and second jaws 160, 170 unless otherwise noted.

Each jaw 160, 170 includes a rounded proximal end 660 that transitions distally into a rectangular cross-section with an openings 662, extending between opposing top and bottom surfaces 666, 668, and having a cylindrical shape configured to receive one of the first and second pins 140, 150. In this fashion, the first and second jaws 160, 170 may be rotationally repositionable with respect to the housing 130 by pivoting about the first and second pins 140, 150. A corresponding cam 600, 602 extends from an interior surface 670 spanning between the top and bottom surfaces 666, 668. The cams 600, 602 engage one another to guide pivoting of the jaws 160, 170 with respect to one another. In exemplary form, the first cam 600 of the first jaw 160 has a rounded rectangular profile but for a U-shaped cavity 674 formed therein, with spaced apart ends 672 that are rounded. This U-shaped cavity 674 is configured to receive a corresponding rounded projection 676 of the second cam 602. Moreover, rounded shoulders 678 of the second cam 602 are configured to engage the rounded ends 672 of the first cam 600 in order to provide corresponding range of motion stops. In particular, the distal most rounded end 672 of the first cam 600 will engage the distal most rounded shoulder 678 of the second cam 602 to limit the pivotal motion of the jaws 160, 170 toward one another. Similarly, the proximal most rounded end 672 of the first cam 600 will engage the proximal most rounded shoulder 678 of the second cam 602 to limit the pivotal motion of the jaws 160, 170 away from one another. In other words, the rounded ends 672 of the first cam 600 do not engage the rounded shoulders 678 of the second cam 602 until an end of the range of motion of the jaws 160, 170 is reached. Conversely, the surface of the first cam 600 delineating the U-shaped cavity 674 is configured to maintain contact with the surface delineating the rounded projection 676 of the second cam 602 through the pivotal range of motion of the jaws 160, 170 with respect to one another.

As part of repositioning the jaws 160, 170 with respect to one another, the proximal end 660 of each jaw includes a cavity 680 that is sized to receive a corresponding pair of pulleys 200, 210. In order to mount the pulleys 200, 210 to the jaws 160, 170, a pair of through openings 682 extends through portions of the jaws, where the through openings 682 are longitudinally aligned. More specifically, the through openings 682 are configured to receive a corresponding third or fourth pin 180, 190 that concurrently extends through the corresponding pulleys 200, 210 in order to mount the pulleys to a jaw. In this exemplary embodiment, each through opening 682 is sized to retain a corresponding pin 180, 190 therein via a friction fit so that the pin does not rotate or move longitudinally with respect to the jaw 160, 170, though fits other than a friction fit may be utilized, while allowing the pulleys 200, 210 to rotate with respect to the pin and jaw. Unlike the second jaw 170, the first jaw 160 includes a through opening 684 extending between the interior surface 670 and an exterior surface 671 of the rectangular-shape profile section. This through opening 684 is sized to receive an end of the control wire 1364 and allow the control wire to pass therethrough, but not so large as to allow an enlarged end of the control wire to pass therethrough. Accordingly, as the control wire 1364 is tensioned, the structure delineating the through opening 684 acts as an anchor to hold an end of the control wire in place. Thus, the pulleys 200, 210 are positioned in a double tackle configuration. As used herein, "tackle" refers to a rope, wire, or other connector section threaded between two blocks, where "block" refers to a pulley mounted on a single axle. As known by those skilled in the art, tackles may be duplicated to create greater and greater mechanical advantage. By way of example, a double tackle configuration comprises four rope sections of the tackles, whereas a luff tackle comprises three rope sections, and a gun tackle comprises two rope sections. In this manner, a luff tackle and a double tackle inherently include a gun tackle. Wires can be single strand metal wire (stainless, music wire, copper, aluminum) or a thin plastic rod made from monofilament flexible plastics such as UHMW, nylon, Teflon, urethane, PET etc., or braided ropes such as metallic (e.g., stainless steel, nitinol, etc.), plastic, and composite.

Though the foregoing exemplary embodiment has been described using four pulleys 200, 210 in a double tackle configuration, it should be noted that other pulley configurations may be used, such as, without limitation, a gun tackle configuration, a watch/Luff tackle configuration, a Gyn tackle configuration, and a three fold purchase configuration, as well as combinations and duplications of the foregoing.

Extending distally past the rectangular cross-section, each jaw 160, 170 includes an arcuate profile that is slightly convex on an exterior surface 692 and concave on an interior surface 690. Opposing top and bottom surfaces 696, 698 are essentially planar and extend parallel to one another. Perimeter surfaces 694 extending between the interior surface 690 and corresponding top and bottom surfaces 696, 698 have an arcuate shape in the longitudinal direction (proximal to distal) and these surfaces cooperate to delineate an interior recess 700 that is sized to receive a corresponding portion of the occlusion clip 102. On the opposite exterior surface 692, a channel 702 is sized and configured to receive a respective deployment wire 1402, 1404 (see FIG. 14), whereas the openings 686 are sized to accommodate throughput of a suture retainer coupled to the occlusion clip 102.

Referring to FIGS. 1-3 and 14, an exemplary assembly sequence for the exemplary end effector 100 will now be described. Initially, the control and deployment wires 1364, 1402, 1404 are routed through the housing 130. Specifically, the wires 1364, 1402, 1404 extend through the longitudinal passage 402 of the housing 130. It should be noted that for simplicity, the deployment wires 1402, 1404 have been omitted from FIGS. 1-3 to show operation of the deployment wire 1364 to open and close the jaws 160, 170.

Each jaw 160, 170 is prepared for mounting to the housing 130 by mounting each jaw to a respective set of pulleys 200, 210. Specifically, the first set of pulleys 200 are inserted into the proximal end cavity 680 so that the openings through the pulleys are aligned with corresponding openings 682 of the first jaw 160. Thereafter, the third pin 180 is inserted into the openings 682 and through the pulleys 200 in order to mount the pulleys to the first jaw 160. Similarly, the second set of pulleys 210 are inserted into the proximal end cavity 680 of the second jaw 170 so that the openings through the pulleys are aligned with corresponding openings 682 of the second jaw. Thereafter, the fourth pin 190 is inserted into the openings 682 and through the pulleys 210 in order to mount the pulleys to the second jaw 170. After the pulleys 200, 210 are mounted to a respective jaw 160, 170, the control wire 1364 is threaded around the pulleys 200, 210 so that a distal enlarged end extends through the opening 684 of the first jaw 160. The control wire 1364 may then be processed (such as by attaching a spherical retainer) to enlarge the distal end prohibiting throughput of an end portion of the control wire through the opening 684. Likewise, the deployment wires 1402, 1404 are directed into corresponding channels 702 (see FIG. 11) of the jaws 160, 170.

Referring to FIGS. 1-3 and 7-15, post preparation, each jaw 160, 170 is mounted to the housing 130. In exemplary form, the interiors of each jaw 160, 170 are oriented to face one another and the openings 662 of each jaw are aligned with a respective through hole 564 of the housing 130. Thereafter, first and second pins 140, 150 are inserted through the holes 564 and through the openings 662 so that the jaws 160, 170 are pivotally mounted to the housing 130. The size of the pins 140, 150 is such that the pins are press fit in the jaws and slip fit with respect to the housing 130, but are not large enough in diameter to inhibit rotation of the jaws 160, 170 when the control wire 1364 is repositioned with respect to the pulleys 200, 210. In this alignment, the cams 600, 602 engage one another to guide rotational repositioning of the jaws 160, 170 with respect to one another. More specifically, the U-shaped cavity 674 of the first cam 600 receives the rounded projection 676 of the second cam 602.

After the jaws 160, 170 have been mounted to the housing 130, the occlusion clip 102 may be mounted to the jaws. In exemplary form, the occlusion clip 102 is oriented so that its parallel beams are longitudinally aligned and inset with respect to the jaws 160, 170, and so that the open end of the occlusion clip is adjacent the open end of the jaws. A series of suture loops 725 (e.g., retainer loops) are longitudinally spaced apart and extend along a length of each beam of the occlusion clip 102, where a portion of each retainer extends through a corresponding opening 686 of an adjacent jaw 160, 170 so that a suture loop 725 extends through each opening 686 and exits on an exterior of a respective jaw. Thereafter, a respective deployment wire 1402, 1404 is fed into a respective channel 702 so that the deployment wire extends through each of the suture loops 725. In this fashion, the occlusion clip 102 is inhibited from detaching from the jaws 160, 170 until the deployment wires 1402, 1404 are withdrawn from the retainer loops, thus allowing the loops to be pulled through the openings 686 to free the occlusion clip from the jaws. And the deployment wires 1402, 1404 along with the control wire 1364 are manipulated via the user control 20.

The following is an exemplary procedure for utilizing the exemplary end effector 100 to deploy the occlusion clip 102 to occlude a left atrial appendage (LAA). Initially, an incision is made on either the left or right side of the chest wall in an intercostal space that is appropriate for the desired angle of approach to a LAA. The incision may be made through the chest wall or through the abdomen (or through the back) as part of various procedures that include, without limitation, an open sternotomy, a left thoracotomy, a right thoracotomy, a left port, a right port, a subxiphoid approach, and a transdiaphragmatic approach. Post incision, a trocar (e.g., 12 millimeter or smaller) may be inserted through the incision to extend into the thoracic cavity. In certain instances, it may be preferred to insufflate the thoracic space subsequent to trocar insertion using known techniques. Using at least one of the incision and trocar, surgical instruments are introduced into the thoracic space in order to perform a series of dissections, including dissection of the pericardium, to provide egress to the LAA. After having access to the LAA, the end effector 100 may be inserted into the thoracic cavity by way of the incision or trocar.

After the end effector 100 is passed through the trocar or incision, the surgeon may utilize a first fenestrated robotic grasper 80 to grasp the outer housing 130. In exemplary form, the first fenestrated robotic grasper 80 may include a pair of bounded openings sized to receive the opposing projections 422 of the outer housing 130. In this fashion, once the robotic grasper 80 grasps the outer housing 130 so that the opposing projections 422 are received within the bounded openings, the robotic grasper controls repositioning of the end effector 100 (but not opening and closing of the jaws 160, 170 or clip 102 deployment from the end effector). As a result, the user controlling the position of the robotic grasper 80 is operative to navigate the end effector 100 (and occlusion clip 102) proximate the LAA. By way of example, the robotic grasper 80 is operative to vary the yaw of the end effector 100 within an X-Y plane, as well as being operative to vary the pitch of the end effector within a Y-Z plane. After navigating the LAA occlusion clip 102 proximate the LAA, the occlusion clip is opened prior to deployment on the LAA.

Opening the LAA occlusion clip 102 is carried out by using a second fenestrated robotic grasper 90. In particular, robotic grasper 90 circumscribes the enlarged end 1365 of the control wire 1364 while the jaws of the robotic grasper sandwich a portion of the control wire therebetween. In this fashion, as the robotic grasper is repositioned away from the proximal end of the outer housing 130, the control wire 1364 is tensioned and pulled proximally. This proximal movement of the control wire 1364 causes the control wire extending between the pulleys 200, 210 to decrease, thereby causing the proximal ends of its jaws 160, 170 to move toward one another. This movement of the proximal ends of the jaws 160, 170 toward one another coincides with the distal ends of the jaws (comprising the far end of the end effector 100) moving away from one another to effectively open the jaws and correspondingly opens the clip 102, which is suture 725 tied to the jaws at this point. Post opening of the LAA occlusion clip 102, the clip is repositioned using the first robotic grasper 80 is repositioned (in concert with the second robotic grasper 90 to maintain the control wire 1364 in tension to maintain the open position of the jaws 160, 170) so that the open end of the occlusion clip is advanced from a side of the LAA, proximate the base of the LAA, until an entire circumference of the LAA interposes corresponding occlusion surfaces of the clip. It should be noted that forceps may be used to grasp a portion of the LAA (proximate the LAA tip) when repositioning the LAA occlusion clip 102 via the robotic grasper 80. After the clip 102 has been positioned at the base of the LAA, with the LAA interposing corresponding occlusion surfaces of the clip, second robotic grasper 90 may be repositioned toward the outer housing 130, which results in a greater amount of control wire between the pulleys 200, 210, thus allowing the proximal ends of the jaws to move away from one another, thereby moving the distal ends of the jaws toward one another and eventually closing the clip 102 to sandwich the LAA between the occlusion clip surfaces. It should be noted that various steps may be undertaken to ensure the entire periphery of a portion of LAA is sandwiched by the clip 102 such as, without limitation, direct visual verification and utilization of a transesophageal echocardiogram. If any problems are determined with respect to clip 102 placement, the opening and closing clip sequence may be repeated along with repositioning of the end effector 100 and clip 102 using the robotic graspers 80, 90 to adjust the positioning of the clip with respect to the LAA. Upon closing the occlusion clip 102 around a periphery of a portion of the LAA, proximate the LAA base, as well as confirming the placement of the closed clip being operative to occlude the LAA, the surgeon may release the clip from the end effector 100.

To release the clip 102 from the end effector 100, the deployment wires 1402, 1404 are repositioned proximally and discontinue engagement with the suture loops 725 that were previously concurrently attached to the deployment clip 102 and the jaws 160, 170. When the engagement between the deployment wires 1402, 1404 and the suture loops 725 is discontinued, the occlusion clip 102 is no longer fastened to the jaws 160, 170 (i.e., the jaws can be opened and closed without repositioning the clip). In exemplary form, after the second robotic grasper 90 is finished with grasping the control wire 1364 to open and close the jaws 160, 170, the second robotic grasper may be utilized to grasp the exposed portions of the deployment wires 1402, 1404 extending proximally from the jaws. The second grasper 90 may grasp one or both deployment wires 1402, 1404 and be pulled away from the outer housing 130 in a straight pull fashion until each wire no longer engages the suture loops 725. After disengagement between the occlusion clip 102 and the end effector 100, the end effector is may be repositioned from proximate the LAA by repositioning the first robotic grasper 80, thereby removing the end effector from the cardiac space.

Removal of the end effector 100 from the patient's body may be controlled via any number of methods. Because the end effector 100 is open-ended, there is no need to reposition the end effector upward along the LAA tip because the end effector can be withdrawn laterally, thus reducing the potential for contact between the end effector and the LAA. In other words, the end effector 100 may be removed from around the LAA without having a tip of the LAA passing between the jaws 160, 170.

Figure 16:
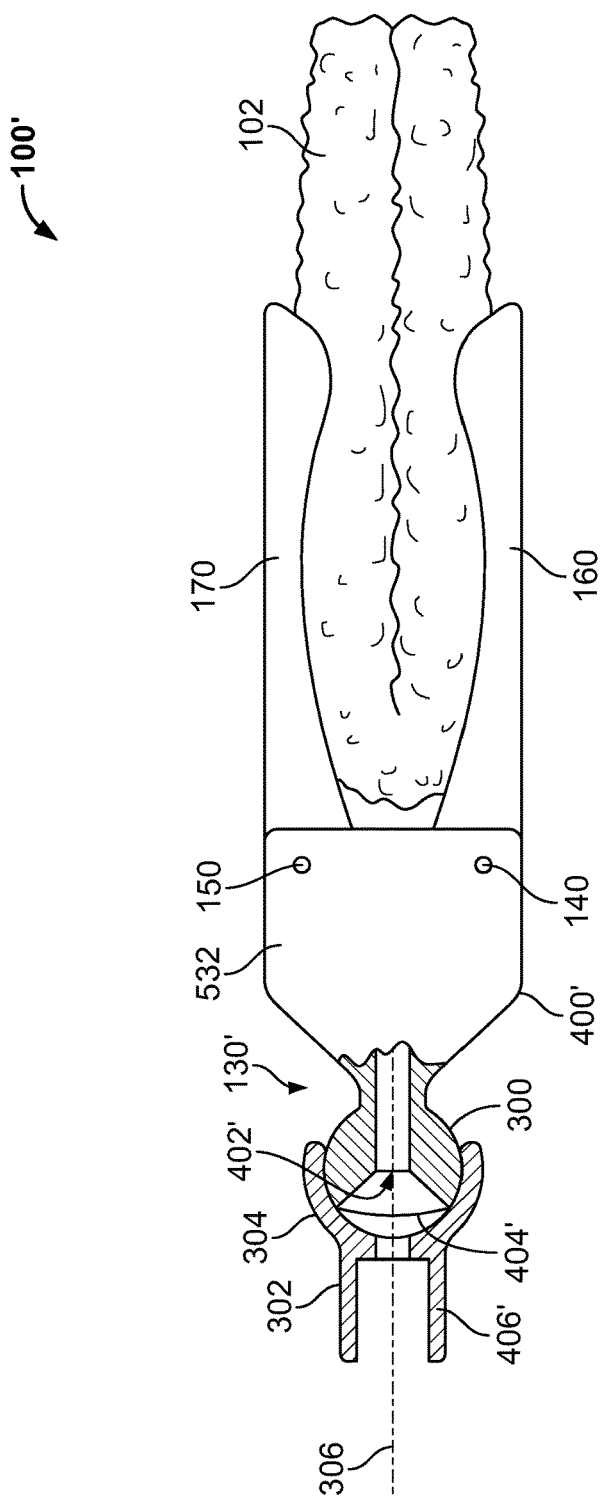
FIG. 16 is a profile view of a first alternate exemplary embodiment of an end effector for deploying an occlusion clip.
Figure 17:
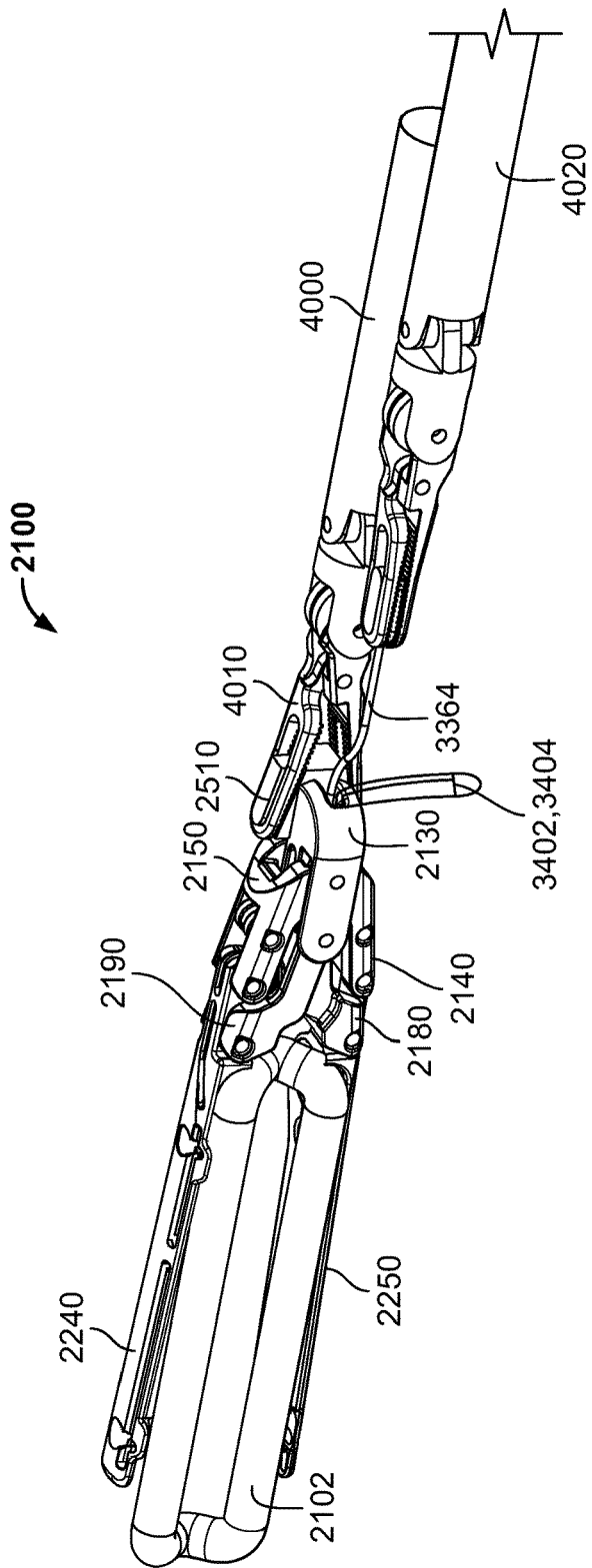
FIG. 17 is an elevated perspective view of a second exemplary end effector for deploying a clip in accordance with the instant disclosure shown mounted to first and second robotic tools with the clip in an open position.
Figure 18:
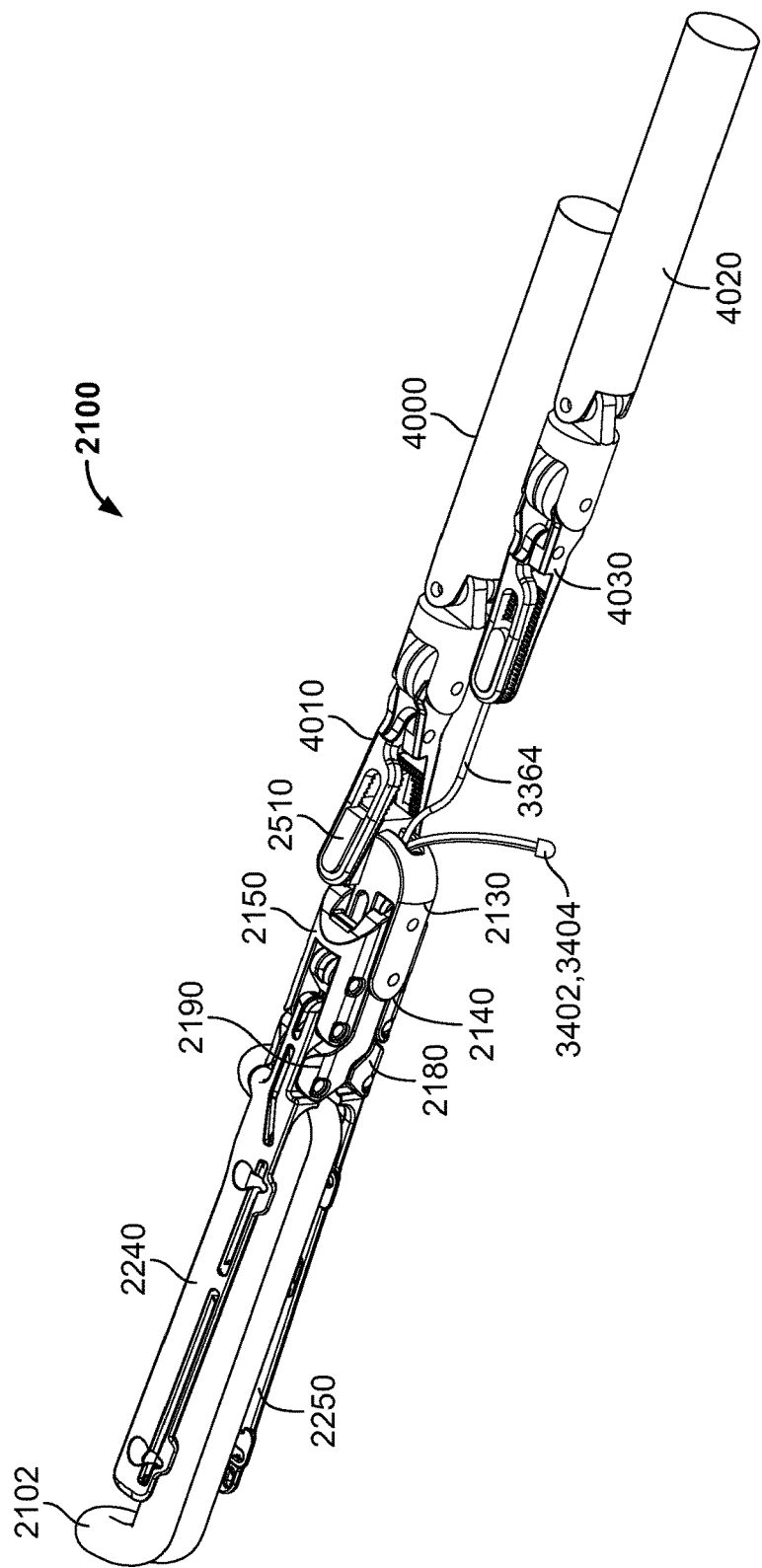
FIG. 18 is an elevated perspective view of the end effector of FIG. 1, with the clip in a closed position.

Turning to FIG. 16, an alternate exemplary end effector 100', which may be utilized in lieu of the first exemplary end effector 100, comprises a two piece housing 130' which is slightly different from the single piece outer housing 130 previously discussed. Unless otherwise noted, the structures of the housings 130, 130' are the same. The housing 130' includes an outer shell 400' that defines a longitudinal passage 402' extending therethrough. A proximal end 404' of the shell 400' that partially delineates the longitudinal passage 402' includes a spherical projection 300 that is repositionable with respect to a receiver 302, which is configured to be grasped by a first fenestrated grasper 80. In exemplary form, the receiver 302 includes a bowl 304 that delineates a semi spherical depression into which the projection 300 is received. More specifically, the projection 300 is repositionably coupled to the receiver 302 so that the projection is rotationally repositionable about an X-axis 306 that extends axially through the receiver 302. In addition, the projection 300 is angularly repositionable with respect to the X-axis 304 between zero and fifty-five degrees. The longitudinal passage 402' is also partially delineated by the receiver 302 in order to allow throughput and repositioning of the deployment wires 1402, 1404 and control wire 1364, which are respectively mounted to the jaws 160, 170 and pulleys 200, 210 (not shown in FIG. 16).

The receiver 302 includes an inner, cylindrical surface 406 that circumscribes a distal end 1390 (see FIG. 3) of the flexible tubing 30 and retains the distal end of the flexible tubing therein via a compression fit or adhesive fit, for example. As was discussed previously, repositioning of the control wire 1364 may result in component motion operative to increase or decrease the distance between the distal ends of the opposing jaws 160, 170 (when the occlusion clip 102 is mounted to the jaws 160, 170, this component motion is also operative to open or close the occlusion clip).

As with the first exemplary housing 130, the receiver 302 of this alternate exemplary housing 103' includes a ledge on its proximal end from which extend opposing projections (not shown). The projections are sized to allow grasping by a surgical grasping and repositioning tool 104, such as a robotic grasper provided as part of the da Vinci surgical system available from Intuitive Surgical. As discussed previously, the surgical grasping and repositioning tool 104 is intended to direct repositioning of the end effector independent of the position of the user control 20 by taking into account the properties of the flexible tube 30.

As with the first exemplary housing 130, the outer shell 400' includes a pair of outer retention arms 530, 532 each including opposed exterior and interior planar surfaces 554, 556, that are bridged laterally by complementary arcuate surfaces 558. A distal most portion of each retention arm 530, 532 includes a planar surface 560 normal to the interior and exterior planar surfaces 554, 556. In this exemplary embodiment, the retention arms 530, 532 have a rounded, rectangular footprint typified by the interior surfaces 556 having a rounded rectangular footprint slightly larger than the exterior surfaces 554 rounded rectangular footprint. Proximate the distal, ninety degree corners of the retention arms 530, 532 are corresponding through holes 564 that extend between the interior and exterior surfaces 554, 556.

As depicted in FIG. 16, analogous to the first exemplary end effector 100, each through hole 564 is sized to receive at least one of the first pin 140 and the second pin 150 in order to pivotally mount a corresponding jaw 160, 170 to the housing 130. In this exemplary embodiment, each through hole 564 is sized to retain a corresponding pin 140, 150 therein via a friction fit (though fits other than a friction fit may be utilized) so that the pin does not rotate with respect to the housing 130, but nonetheless the jaws 160, 170 rotate about the pins 140, 50. It should be noted that alternatively, for example, the through holes 564 may be sized to allow rotation of a corresponding pin 140, 150 therein so that the pins and jaws 160, 170 rotate together with respect to the housing 130 (in which case the pin 140, 150 received by a respective jaw 160, 170 may not be independently rotationally repositionable with respect to that jaw).

An exemplary assembly sequence for the alternate exemplary end effector 100' includes mounting the outer shell 400' to the receiver 302. More specifically, the projection 300 of the outer shell 400' is received within the bowl 304 to create a snap-fit connection as a result of the bowl circumscribing more than 180 degrees of the spherical projection. Yet in this snap-fit connection, the projection 300 is repositionably coupled to the receiver 302 so that the projection is rotationally repositionable about the X-axis 304 and angularly repositionable with respect to the X-axis 304 between zero and fifty-five degrees. Post mounting the outer shell 400' to the receiver 302, the control and deployment wires 1364, 1402, 1404 may be routed through the housing 130' along the longitudinal passage 402' and through the flexible tube 30. Specifically, the wires 1364, 1402, 1404 extend through the longitudinal passage 402' of the housing 130', through the hollow flexible tube 30, and into the interior of the user control 20.

Each jaw 160, 170 is prepared for mounting to the outer shell 400' of the housing 130' by mounting each jaw to a respective set of pulleys 200, 210. Specifically, the first set of pulleys 200 are inserted into the proximal end cavity 680 so that the openings through the pulleys are aligned with corresponding openings 682 of the first jaw 160. Thereafter, the third pin 180 is inserted into the openings 682 and through the pulleys 200 in order to mount the pulleys to the first jaw 160. Similarly, the second set of pulleys 210 are inserted into the proximal end cavity 680 of the second jaw 170 so that the openings through the pulleys are aligned with corresponding openings 682 of the second jaw. Thereafter, the fourth pin 190 is inserted into the openings 682 and through the pulleys 210 in order to mount the pulleys to the second jaw 170. After the pulleys 200, 210 are mounted to a respective jaw 160, 170, the control wire 1364 is threaded around the pulleys 200, 210 so that a distal end extends through the opening 684 of the first jaw 160. The control wire 1364 may then be processed (such as by attaching a spherical retainer) to enlarge the distal end prohibiting throughput of an end portion of the control wire through the opening 684. Likewise, the deployment wires 1402, 1404 are directed into corresponding channels 702 of the jaws 160, 170.

Post preparation, each jaw 160, 170 is mounted to the outer shell 400' of the housing 130'. In exemplary form, the interiors of each jaw 160, 170 are oriented to face one another and the openings 662 of each jaw are aligned with a respective through hole 564 of the outer shell 400'. Thereafter, first and second pins 140, 150 are inserted through the holes 564 and through the openings 662 so that the jaws 160, 170 are pivotally mounted to the outer shell 400'. The size of the pins 140, 150 is such that the pins frictionally fit with respect to the outer shell 400', but are not large enough in diameter to inhibit rotation of the jaws 160, 170 when the control wire 1364 is repositioned with respect to the pulleys 200, 210. In this alignment, the cams 600, 602 engage one another to guide rotational repositioning of the jaws 160, 170 with respect to one another. More specifically, the U-shaped cavity 674 of the first cam 600 receives the rounded projection 676 of the second cam 602.

After the jaws 160, 170 have been mounted to the outer shell 400', the occlusion clip 102 may be mounted to the jaws. In exemplary form, the occlusion clip 102 is oriented so that its parallel beams are longitudinally aligned and inset with respect to the jaws 160, 170, and so that the open end of the occlusion clip is adjacent the open end of the jaws. A series of suture loops 725 (e.g., retainer loops) are longitudinally spaced apart and extend along a length of each beam of the occlusion clip 102, where a portion of each retainer extends through a corresponding opening 686 of an adjacent jaw 160, 170 so that a suture loop 725 extends through each opening 686 and exits on an exterior of a respective jaw. Thereafter, a respective deployment wires 1402, 1404 is fed into a respective channel 702 so that the deployment wire extends through each of the suture loops 725. In this fashion, the occlusion clip 102 is inhibited from detaching from the jaws 160, 170 until the deployment wires 1402, 1404 are withdrawn from the retainer loops, thus allowing the loops to be pulled through the openings 686 to free the occlusion clip from the jaws. And the deployment wires 1402, 1404 along with the control wire 1364 are manipulated via the user control 20.

Consistent with the foregoing exemplary discussion for utilizing the first exemplary end effector 100, the second exemplary end effector 100' may be similarly utilized in lieu of the first exemplary end effector 100 and, consequently, a detailed explanation of utilizing the second exemplary end effector 100 has been omitted in furtherance of brevity.

Referring to FIGS. 17-40, an exemplary end effector 2100 may be used in minimally invasive surgical procedures to allow deployment of an LAA occlusion clip 2102 with respect to a left atrial appendage (not shown). United States Patent Application Publication number 2012/0059400, which describes an exemplary LAA occlusion clip 2102, is incorporated herein by reference. As will be apparent to those skilled in the art after reviewing the instant disclosure, the end effector 2100 may be utilized in capacities other than LAA occlusion clip deployment, each of which is within the scope of this disclosure.

The end effector 2100 comprises a linkage housing 2130, where a medial portion of the linkage housing 2130 has mounted to it a first pin 2160 that extends through a first drive link 2140 and a second drive link 2150. In this fashion, the first drive link 2140 and the second drive link 2150 are rotatably repositionable with respect to the linkage housing 2130 and with respect to one another along a common axis longitudinally aligned with the first pin 2160. A distal portion of the linkage housing 2130 has mounted to it a second pin 2170 and a third pin 2230 that extends through proximal ends of a first parallel link 2180 and a second parallel link 2190. In this fashion, the first parallel link 2180 and the second parallel link 2190 are rotatably repositionable with respect to the linkage housing 2130 and with respect to one another along a common axis longitudinally aligned with the second and third pins 2170, 2230.

Interposing the proximal ends of the first and second parallel links 2180, 2190 are a first toggle 2200, a second toggle 2210, and a pulley 2220. The pulley 2220 includes a pair of cylindrical projections extending in opposite directions along a rotational axis of the pulley, where the first toggle 2200 is mounted to a first of the cylindrical projections and the second toggle 2210 is mounted to a second of the cylindrical projections. A distal end of the first drive link 2140 is mounted to a proximal end of a first jaw 2240, whereas a distal end of the second drive link 2150 is mounted to a proximal end of a second jaw 2250. In this fashion, the first drive link 2140 is rotatably repositionable with respect to the first jaw 2240 along a common axis longitudinally aligned with a fifth pin 2260 that concurrently extends through the first drive link and the first jaw. Similarly, the second drive link 2150 is rotatably repositionable with respect to the second jaw 2250 along a common axis longitudinally aligned with a sixth pin 2270 that concurrently extends through the second drive link and the second jaw.

Near the proximal end of the first jaw 2240, inset distally from the location where the first drive link 2140 is mounted, the distal end of the first parallel link 2180 is mounted to the first jaw. In this fashion, the first parallel link 2180 is rotatably repositionable with respect to the first jaw 2240 along a common axis longitudinally aligned with a seventh pin 2290 that concurrently extends through the first parallel link and the first jaw. In corresponding fashion, the proximal end of the second jaw 2250, inset distally from the location where the second drive link 2150, is mounted to the distal end of the second parallel link 2190. Similarly, the second parallel link 2190 is rotatably repositionable with respect to the second jaw 2250 along a common axis longitudinally aligned with an eighth pin 2300 that concurrently extends through the second parallel link and the second jaw.

In this exemplary end effector 2100, the jaws 2240, 2250 are repositioned toward and away from one another while maintaining a parallel orientation. In order to reposition the first and second jaws 2240, 2250 with respect to one another, the first and second drive links 2140, 2150 as well as the first and second parallel links 2180, 2190 are rotated with respect to the linkage housing 2130. To facilitate this repositioning of the jaws 2240, 2250 with respect to one another, the distal ends of the first and second toggles 2200, 2210 are mounted to medial portions of respective drive links 2140, 2150. In particular, the distal end of the first toggle 2200 is mounted to a medial portion of the first drive link 2140 via a ninth pin 2310. Accordingly, the first toggle 2200 is rotatably repositionable with respect to the first drive link 2140 along a common axis longitudinally aligned with the ninth pin 2310. In addition, the distal end of the second toggle 2210 is mounted to a medial portion of the second drive link 2150 via a tenth pin 2320. Consequently, the second toggle 2210 is rotatably repositionable with respect to the second drive link 2150 along a common axis longitudinally aligned with the tenth pin 2320. A more detailed discussion of the component parts of the end effector 2100 follows.

Figure 20:
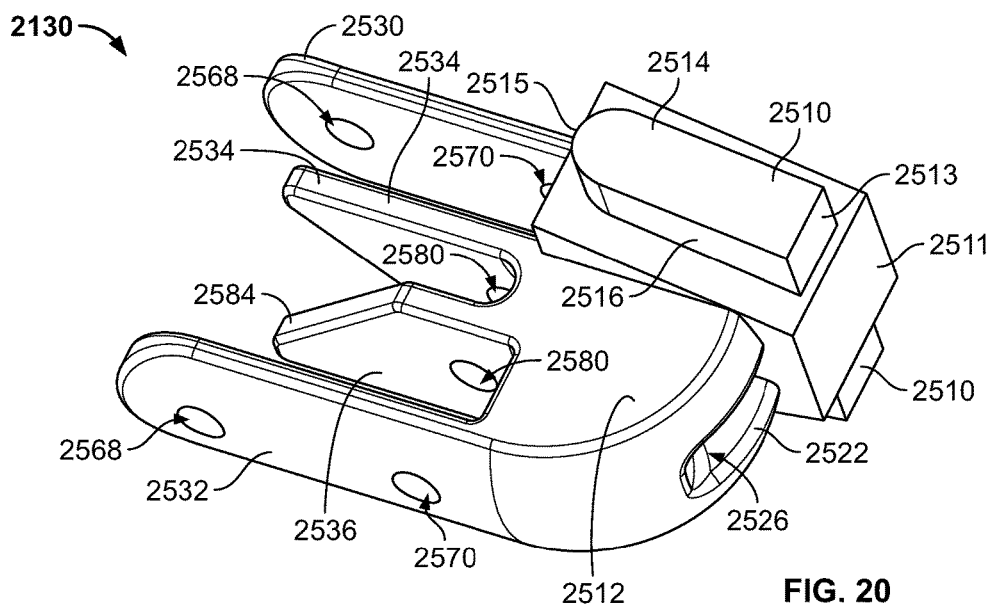
FIG. 20 is an elevated perspective view from a proximal end of an exemplary linkage housing in accordance with the instant disclosure.
Figure 21:
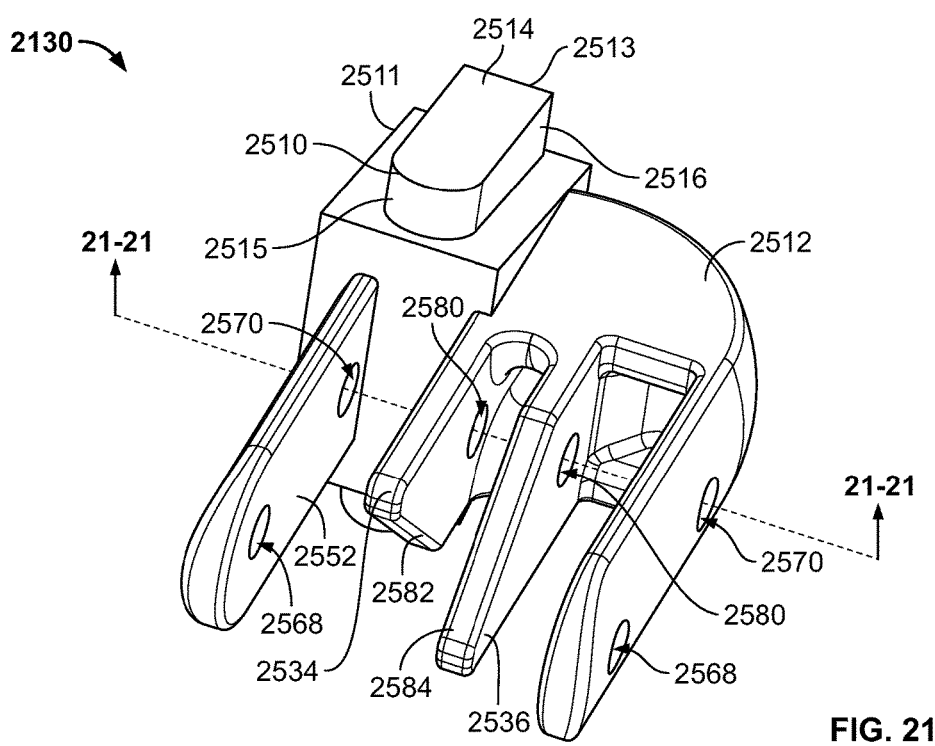
FIG. 21 is an elevated perspective view from a distal end of the exemplary linkage housing of FIG. 20.
Figure 22:
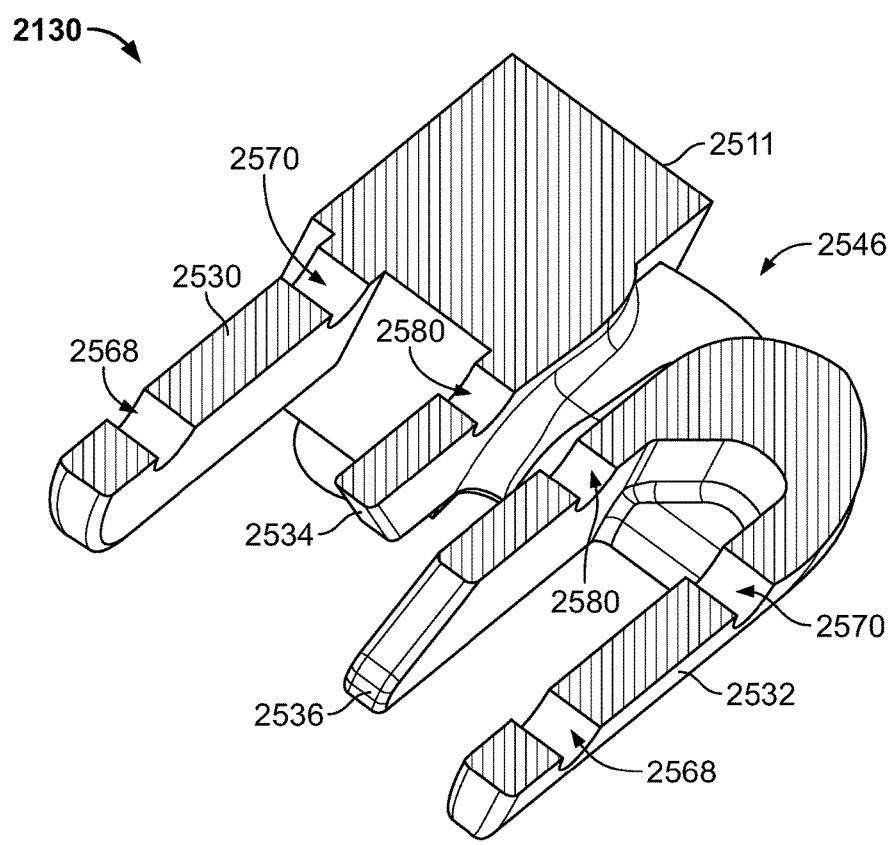
FIG. 22 is a cross-sectional view of the exemplary linkage housing of FIG. 21 taken along line 21-21.
Figure 23:
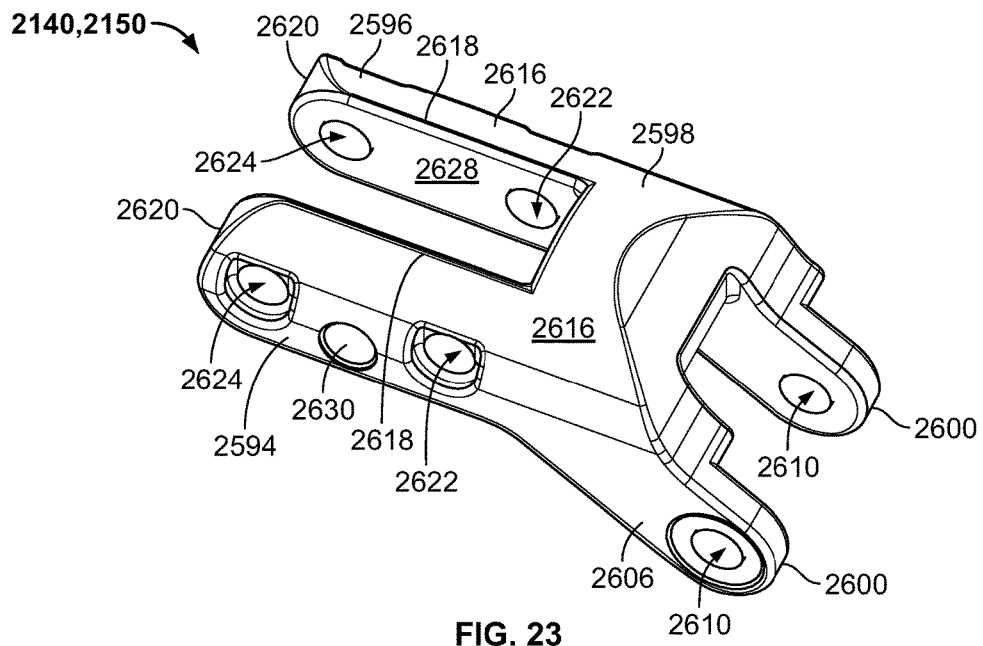
FIG. 23 is an elevated perspective view from a proximal end of an exemplary drive link in accordance with the instant disclosure.
Figure 24:
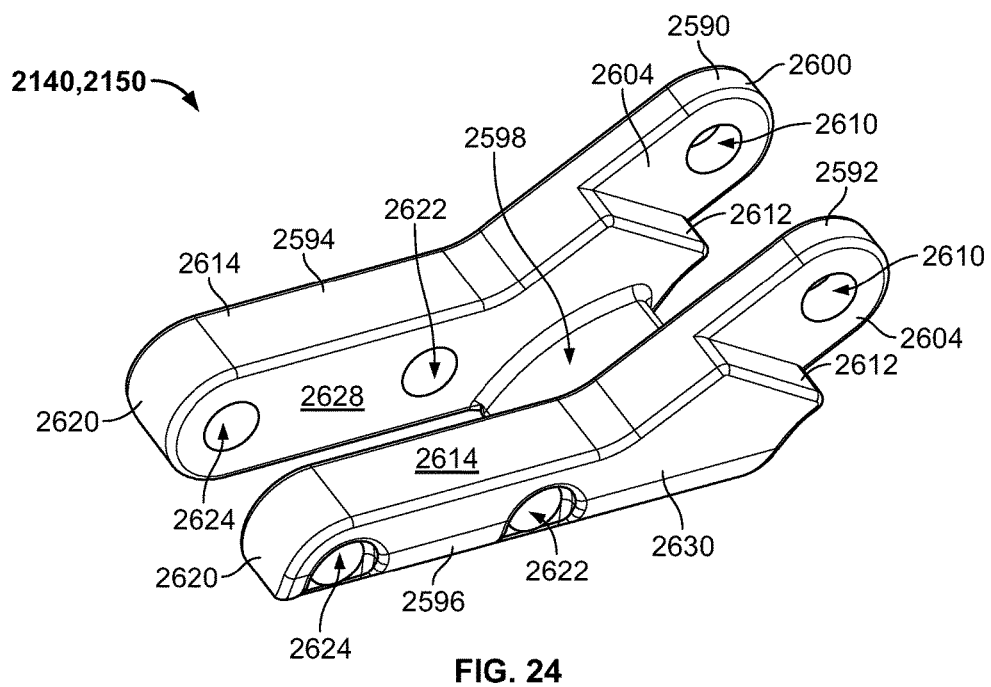
FIG. 24 is an elevated perspective view from a distal end of the exemplary drive link of FIG. 23.
Figure 25:
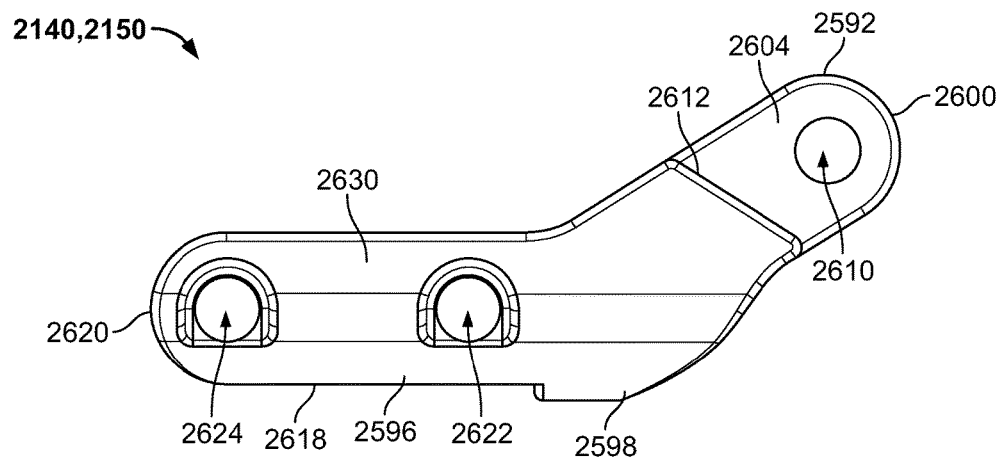
FIG. 25 is a profile view of the exemplary drive link of FIG. 23.

As shown in FIGS. 20-22, the linkage housing 2130 includes a pair of elongated projections 2510 extending outward from a trapezoidal block 2511 extending laterally, proximally, and distally offset from a midline and from opposing top and bottom exterior surfaces 2512 of the linkage housing. In this exemplary embodiment, the projections 2510 include a plateau surface 2514 that is generally planar and angled other than parallel with respect to the planar top/bottom surface 2512. A peripheral shape of each projection 2510 is rectangular on a proximal end 2513 and is rounded on a distal end 2515 and generally centered with respect to the trapezoidal block 2511. In particular, a peripheral surface 2516 of each projection 2510 has a substantially constant height from distal to proximal to provide a uniform height of the projection 2510 proximal to distal.

A proximal end 2522 of the linkage housing 2130 is semicircular in profile. In particular, the proximal end 2522 includes a miniature channel 2526 that terminates at a corresponding through opening 2546 extending into an interior of the linkage housing 2130. The through opening 2546 extends distally and terminates in between a pair of inner arms 2534, 2536. The central through opening 2546 is sized to accommodate a control wire 3364 coupled to the pulley 2220 (see FIG. 17). As will be discussed in more detail hereafter, repositioning of the pulley 2220 with respect to the linkage housing 2130 results in component motion operative to increase or decrease the distance between the opposing jaws 2240, 2250 responsive to components being pivotally connected to a pair of outer retention arms 2530, 2532 and the inner arms 2534, 2536.

In exemplary form, the outer retention arms 2530, 2532 each include a respective interior wall surface 2552 that provides a camming surface against which the parallel links 2180, 2190 rotate. In this exemplary embodiment, the interior wall surfaces 2552 are planar and parallel to one another. A distal orifice 2568 extends through the entire outer retention arm 2530, 2532. The distal orifice 2568 is sized to accommodate one of the second pin 2170 and the third pin 2230 in order to allow pivotal motion between the linkage housing 2130 and the parallel links 2180, 2190. By way of example, the distal orifices 2568 of the outer retention arms 2530, 2532 are cylindrical and have axial centers that lie along a common axis. In addition to the distal orifice, each outer retention arm 2530, 2532 also includes a proximal orifice 2570 that extends entirely through the outer retention arm. The proximal orifice 2570 is sized to accommodate the first pin 2160 in order to allow pivotal motion between the linkage housing 2130 and the drive links 2140, 2150. By way of example, the proximal orifices 2570 of the outer retention arms 2530, 2532 are cylindrical and have axial centers that lie along a common axis.

The inner arms 2534, 2536 extend distally and are generally parallel with the outer retention arms 2530, 2532, with spacing between each set of adjacent arms. In exemplary form, the inner arms 2534, 2536 each include a single hole 2580 that extends laterally through the arm and is cylindrical in shape. A central axis extending through each hole 2580 is coaxial with the counterpart central axis of the other hole. Likewise, the central axis of the holes 2580 is coaxial with the common axis of the proximal orifices 2570 so that the holes and orifices are sized to accommodate the first pin 2160 in order to allow pivotal motion between the linkage housing 2130 and the drive links 2140, 2150 (compare FIGS. 17 and 18). The spacing between the arms 2534, 2536 allows for proximal-to-distal motion of the pulley 2220 therebetween, while prohibiting motion of the toggles 2200, 2210 therebetween. Rather, the first arm 2534 includes a triangular projection extending distally, the hypotenuse of which comprises a first surface 2582 that is angled to generally face the top surface 2512. Similarly, the second arm 2536 includes a triangular projection extending distally, the hypotenuse of which comprises a second surface 2584 that is angled to generally face the bottom surface 2512. In this exemplary embodiment, the surfaces 2582, 2584 are perpendicular to one another and, as will be discussed in more detail hereafter, the toggles 2200, 2210 contact these surfaces in order to limit repositioning of the toggles as the pulley 2220 is repositioned.

Referencing FIGS. 19 and 23-25, the first and second drive links 2140, 2150 as well as the first and second parallel links 2180, 2190 are rotationally repositionable and mounted to the linkage housing 2130. In exemplary form, the first and second drive links 2140, 2150 are structurally identical, but differ only in operation based upon the components mounted thereto. Consequently, the following discussion of the structure of a drive link is applicable to both the first and second drive links 2140, 2150.

Each drive link 2140, 2150 comprises a unitary structure including a pair of spaced apart, tilted uprights 2590, 2592 that are angled approximately forty-five degrees with respect to corresponding longitudinal extensions 2594, 2596. The base of the uprights 2590, 2592 are joined to one another via a bridge 2598. In exemplary form, each upright 2590, 2592 includes a rounded proximal end 2600 that interposes opposing planar surfaces 2604, 2606. Extending completely through each upright 2590, 2592 is a hole 2610 partially bounded by the opposing planar surfaces 2604, 2606 and having a cylindrical shape that is sized to accommodate throughput of the first pin 2160 and allow rotational repositioning of each upright around the first pin. Each upright 2590, 2592 also includes a step 2612 recessed distally beyond the proximal end 2600 and the hole 2610. The step 2612, as will be discussed in more detail hereafter, is inset to approximately half of the thickness of the widest portion of the upright 2590, 2592. Extending distally from the step 2612, each upright 2590, 2592 seamlessly transitions into a respective longitudinal extension 2594, 2596. The bridge 2598 is positioned approximate the transition region between the uprights 2590, 2592 and the longitudinal extensions 2594, 2596 and recessed with respect to bottom planar surfaces 2614 of the longitudinal extensions. On the top side 2616 of each drive link 2140, 2150, the bridge 2598 seamlessly transitions into the longitudinal extensions 2594, 2596 an embodies an arcuate, convex longitudinal profile so that the top of each longitudinal extension includes a longitudinal ridge 2618 extending from the bridge 2598 distally toward a distal rounded end 2620 of each longitudinal extension. Along the longitudinal length of each longitudinal extension 2594, 2596 is a pair of openings 2622, 2624 extending completely through the longitudinal extensions between opposing lateral inner and exterior sides 2628, 2630. Each opening 2622, 2624 has a cylindrical shape and is configured to receive at least one of the fifth, sixth, ninth, and tenth pins 2260, 2270, 2310, 2320. In this fashion, the first and second toggles 2200, 2210 as well as the first and second jaws 2240, 2250 may be rotationally repositionable with respect to one of the drive links 2140, 2150.

Referring to FIGS. 19 and 32-34, the first and second toggles 2200, 2210 as well as the first and second jaws 2240, 2250 are rotationally repositionable and mounted to the drive links 2140, 2150. In exemplary form, the first and second toggles 2200, 2210 are structurally identical, but differ only in operation based upon the components mounted thereto. Consequently, the following discussion of the structure of a toggle is applicable to both the first and second toggles 2200, 2210.

Each toggle 2200, 2210 comprises a unitary structure including toggle connector portion 2640 and a drive link connector portion 2642. In exemplary form, the toggle connector portion includes a rounded end 2644 with a substantially constant width that is approximately half of the width of the drive link connector portion 2642. Along the longitudinal length of the toggle connector portion 2640, an arcuate profile exists. This toggle connector portion 2640 includes a through opening 2646 having a cylindrical shape and configured to receive a cylindrical projection of the pulley 2220 so that the toggle 2200, 2210 is rotationally repositionable about the pulley 2220.

Opposite the toggle connector portion 2640, the drive link connector portion 2642 includes an offset 2648 extending widthwise beyond the width of the toggle connector. An opening 2650 extends through the drive link connector portion 2642 and the offset 2648 having a cylindrical shape and configured to receive one of the ninth and tenth pins 2310, 2320 so that the toggle 2200, 2210 is rotationally repositionable about a drive link 2140, 2150. A partial circumferential groove 2652 exists on the rounded end 2654 of the drive link connector portion 2642. This groove 2652 is configured to receive a portion of a deployment wire 3402, 3404 (see FIG. 39) in order to allow the deployment wire to contact and be unimpeded by motion of the toggle 2200, 2210 when the toggle is repositioned and/or when the deployment wire is repositioned with respect to the jaws 2240, 2250 in order to detach, for example, a left atrial occlusion clip 2102 temporarily mounted to the jaws.

Figure 26:
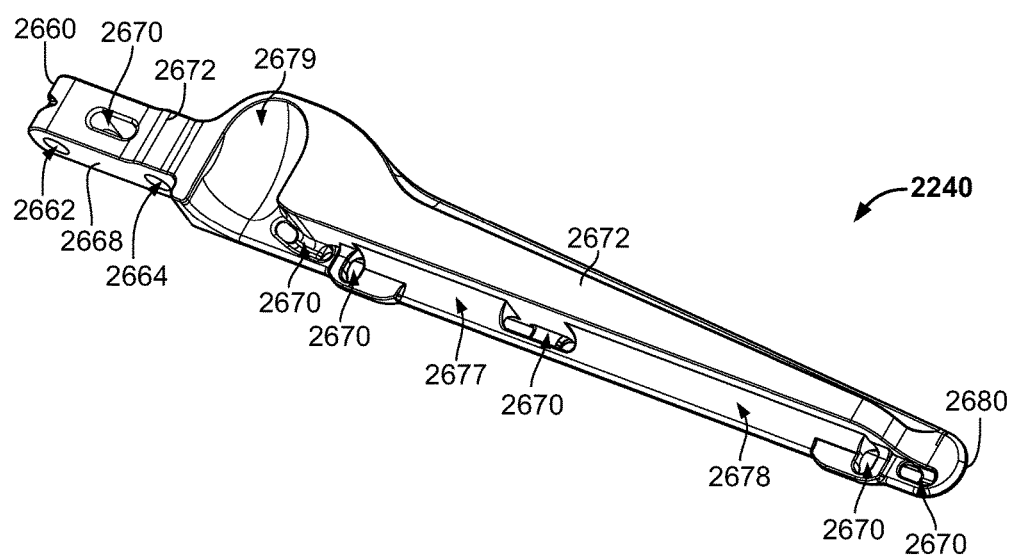
FIG. 26 is an elevated perspective view from a distal end of a first jaw in accordance with the instant invention.
Figure 27:
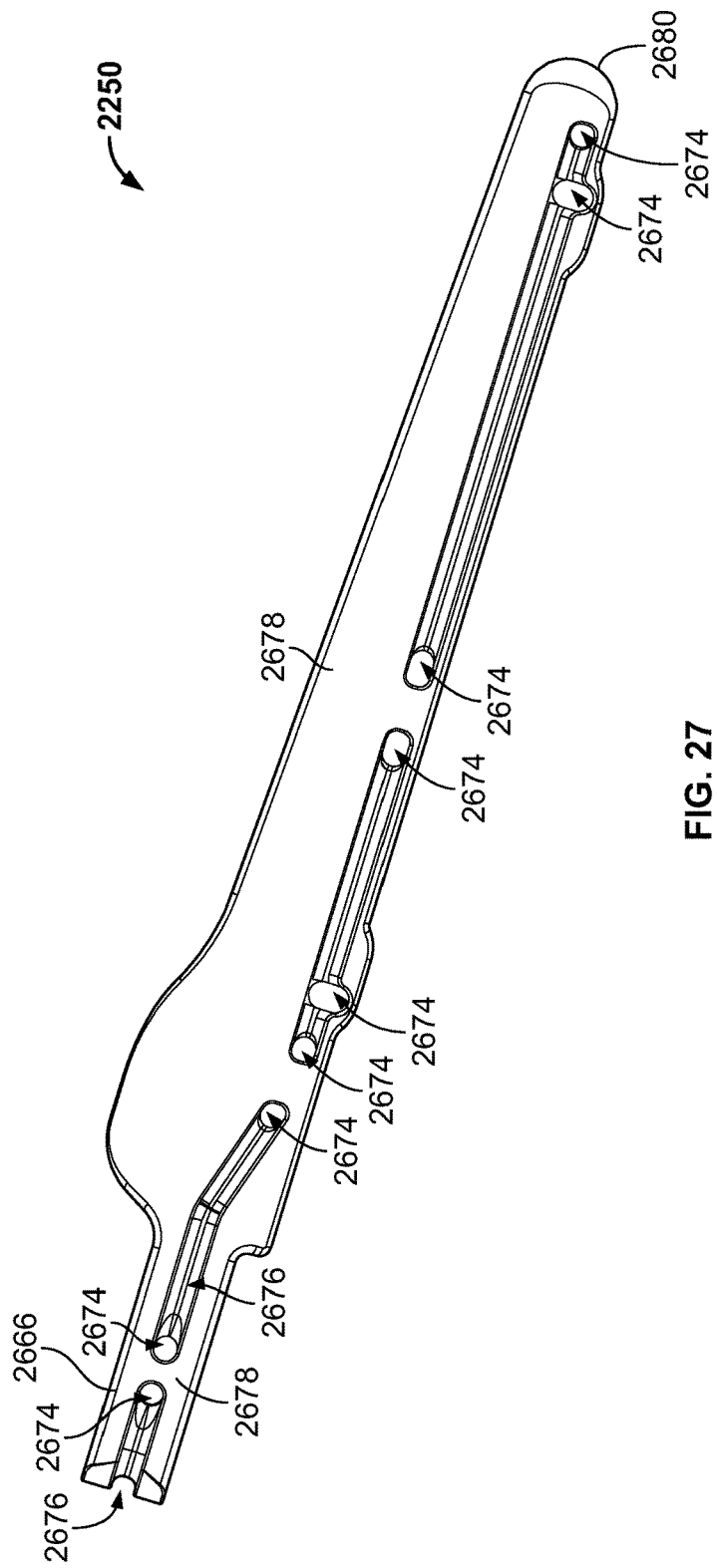
FIG. 27 is profile view of a second jaw in accordance with the instant invention.
Figure 28:
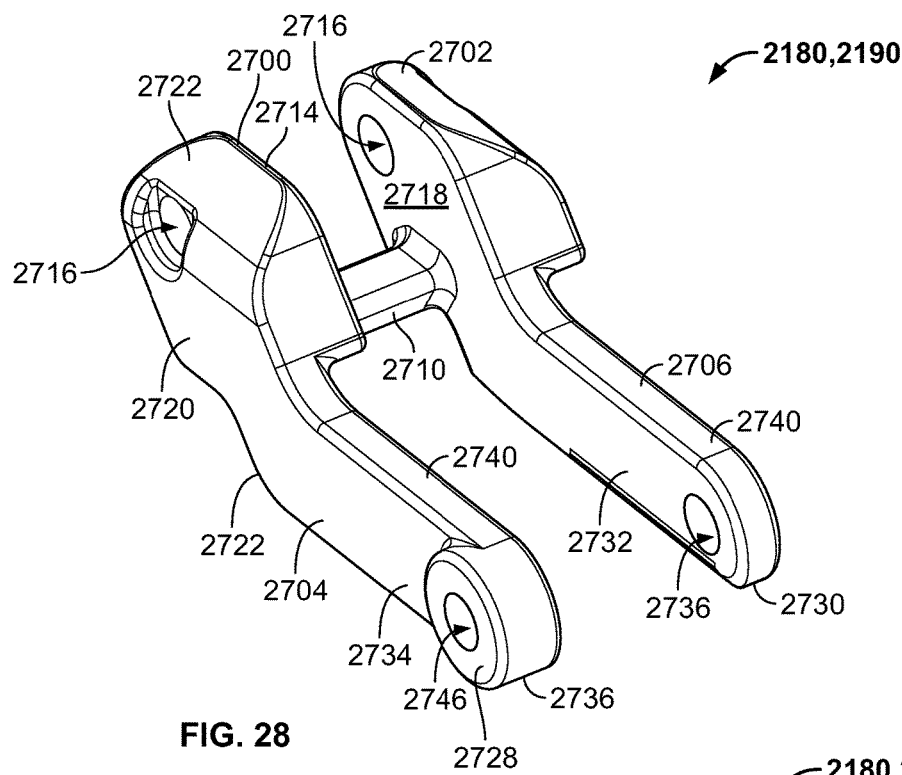
FIG. 28 is an elevated perspective view from a proximal end of an exemplary parallel link in accordance with the instant disclosure.
Figure 29:
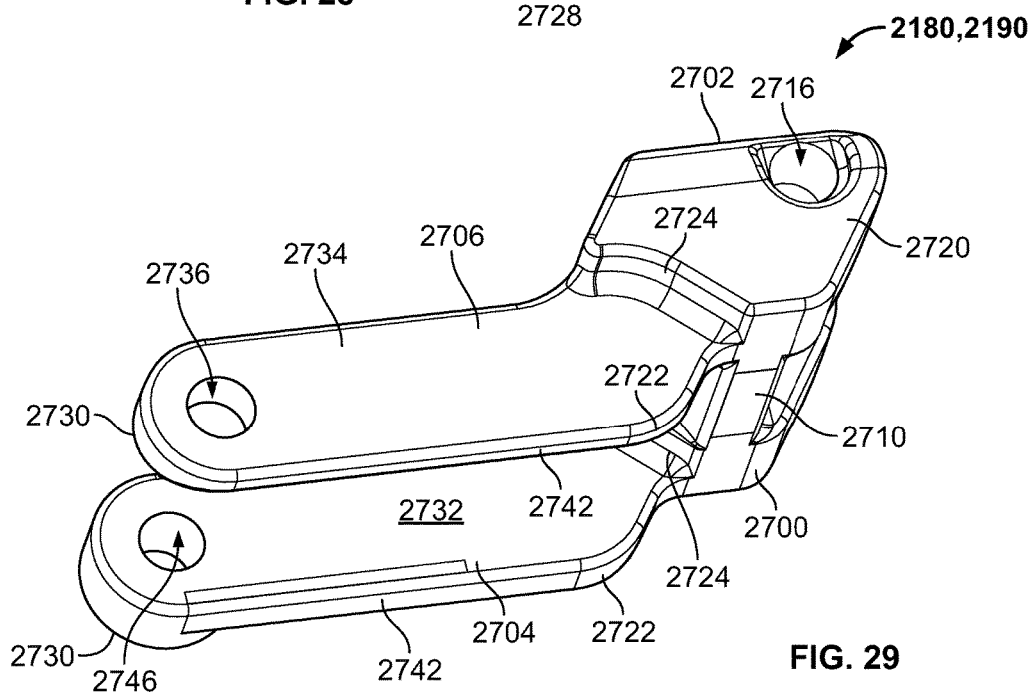
FIG. 29 is an elevated perspective view from a side of the exemplary parallel link of FIG. 28.
Figure 30:
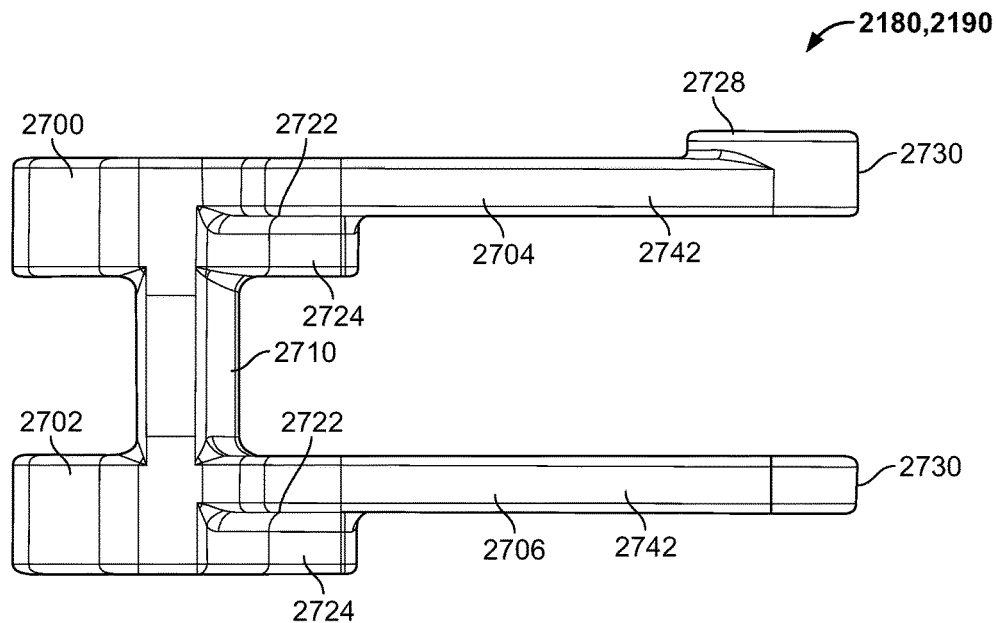
FIG. 30 is a bottom view of the exemplary parallel link of FIG. 28.

As shown in FIGS. 26 and 27, the jaws 2240, 2250 are structurally mirror images of one another. Consequently, the following discussion of the structure of a jaw is generally applicable to both the first and second jaws 2240, 2250.

Figure 19:
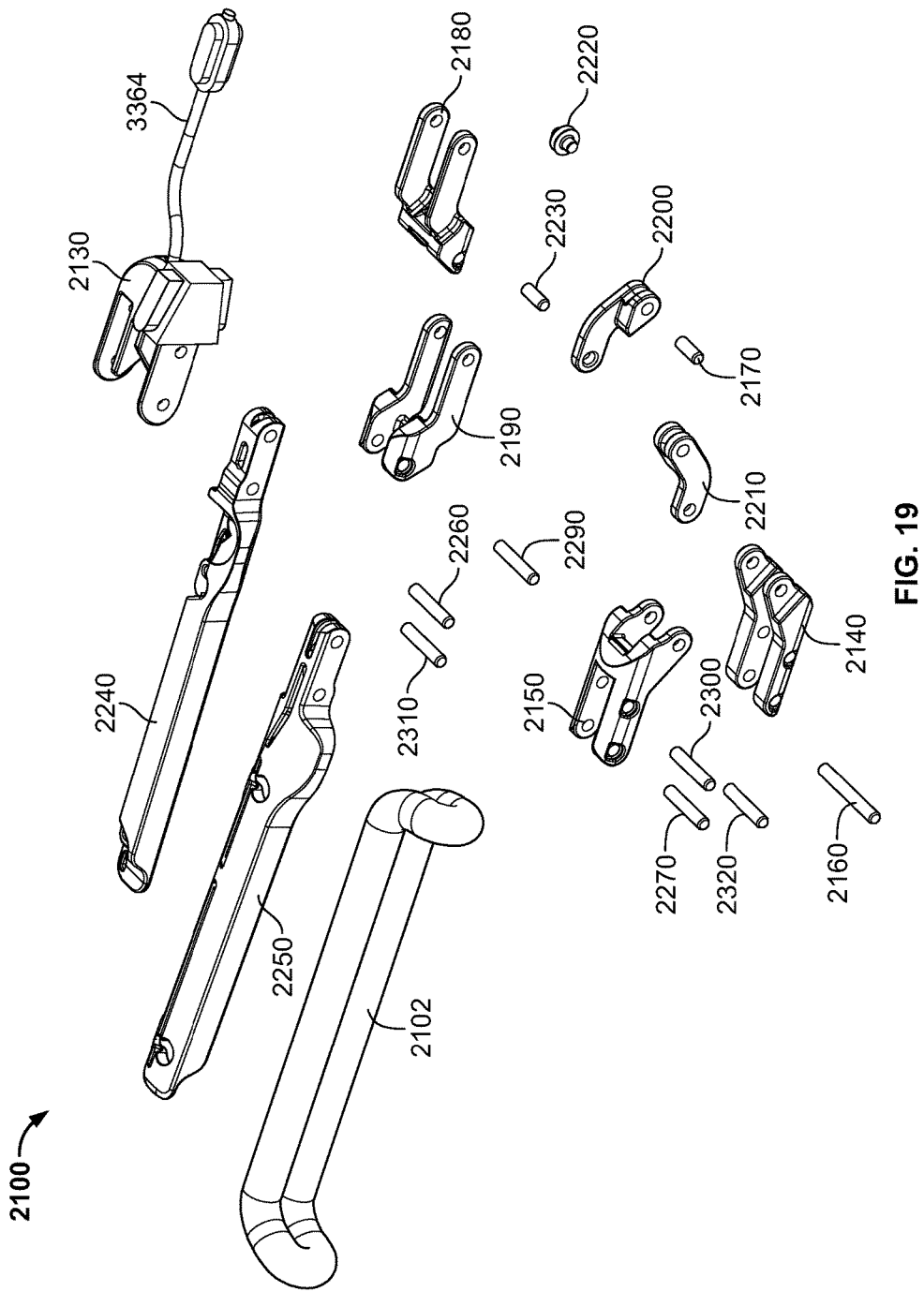
FIG. 19 is an exploded view of the end effector of FIGS. 1 and 2 with the occlusion clip.

Each jaw 2240, 2250 includes a rounded proximal end 2660 that transitions distally into a rectangular cross-section with a pair of openings 2662, 2664 extending between opposing top and bottom surfaces 2666, 2668 each having a cylindrical shape and being configured to receive at least one of the fifth, sixth, seventh, and eighth pins 2260, 2270, 2290, 2300 (see FIG. 19). In this fashion, the first and second jaws 2240, 2250 may be rotationally repositionable with respect to the drive links 2140, 2150 and the parallel links 2180, 2190. The rectangular cross-section also includes one of a series of openings 2670 on an interior surface 2672 in communication with a plurality of openings 2674 and channels 2676 formed into the opposing exterior surface 2678. In this exemplary embodiment, the channels 2676 are sized and configured to receive a respective deployment wire 3402, 3404, whereas the openings 2670, 2674 are sized to accommodate throughput of a suture retainer coupled to the left atrial occlusion clip 2102. The interior surface 2672 also has formed therein a LAA spring depression 2676 sized and configured to receive a biasing spring of the left atrial occlusion clip 2102 (see FIG. 37). This LAA spring depression 2679 is in communication with a longitudinal depression 2677 formed into the interior surface 2672 and the bottom surface 2668. And this longitudinal depression 2677 is sized and configured to receive occlusion bars of the left atrial occlusion clip 2102. Each jaw 2240, 2250 tapers longitudinally from proximal to distal after passing beyond the LAA spring depression 2679 to terminate at a rounded distal end 2680. As part of repositioning the jaws 2240, 2250 with respect to one another, the parallel links 2180, 2190 are also repositioned with respect to one another.

Referring to FIGS. 19 and 28-31, the first and second parallel links 2180, 2190 are structurally identical, but differ only in operation based upon the components mounted thereto. Consequently, the following discussion of the structure of a parallel link is applicable to both the first and second parallel links 2180, 2190.

Figure 31:
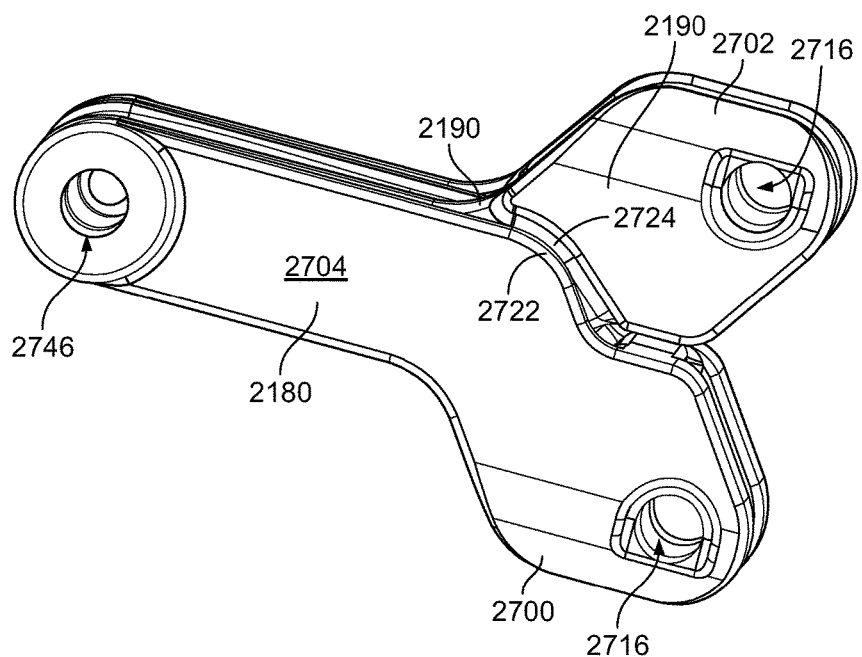
FIG. 31 is an elevated perspective view from a side showing the exemplary parallel links aligned with one another in a compact position.
Figure 32:
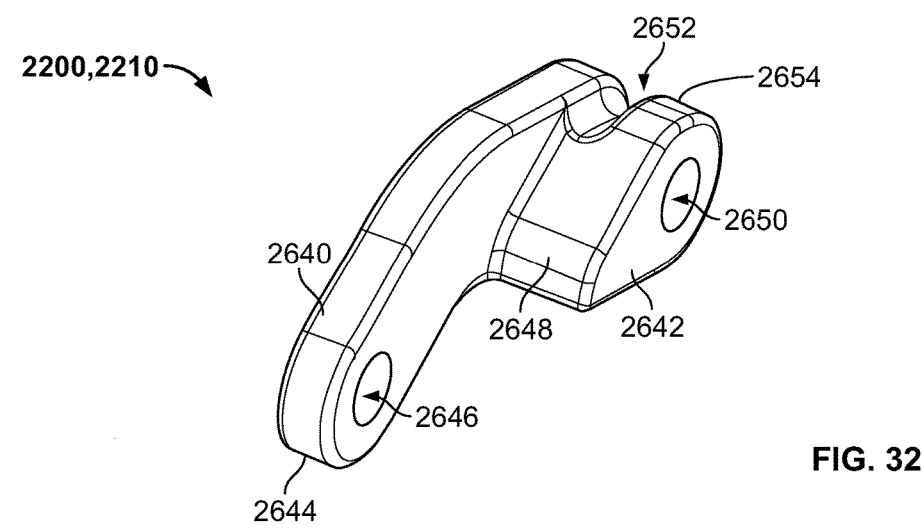
FIG. 32 is an elevated perspective view from a distal end of an exemplary toggle in accordance with the instant disclosure.
Figure 33:
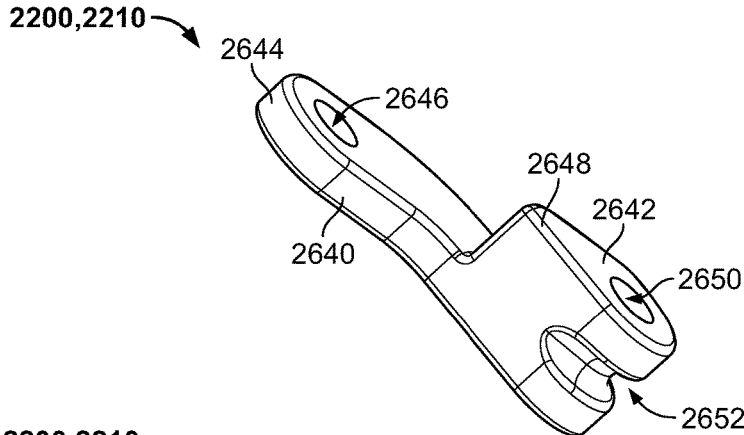
FIG. 33 is an elevated perspective view from a bottom of the exemplary toggle of FIG. 32.
Figure 34:
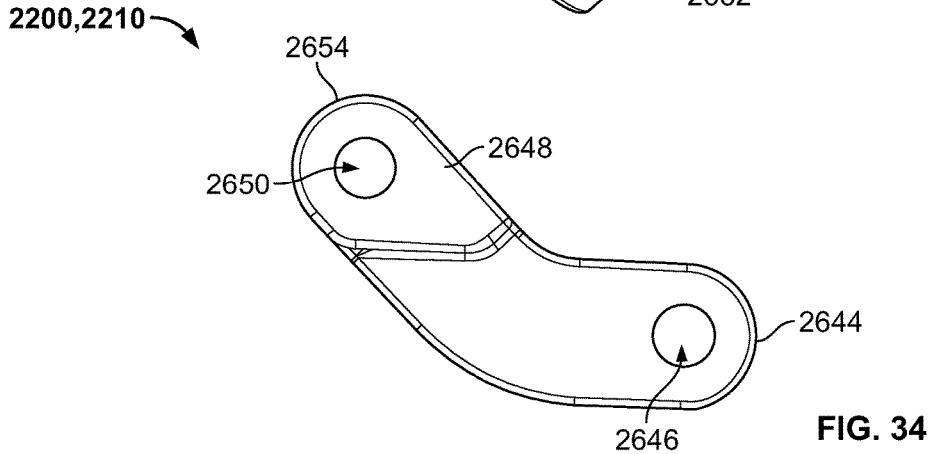
FIG. 34 is a profile view of the exemplary toggle of FIG. 32.
Figure 35:
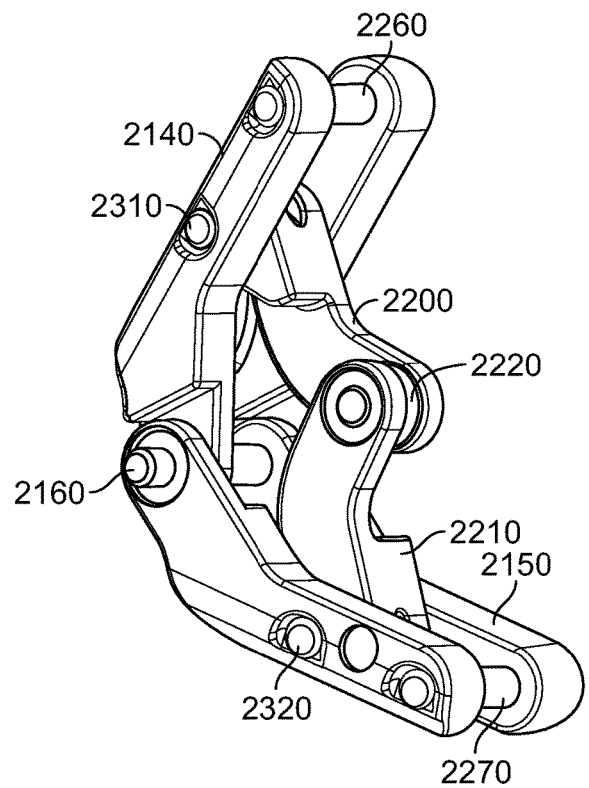
FIG. 35 is an elevated perspective view showing assembly of the toggles and drive links.
Figure 36:
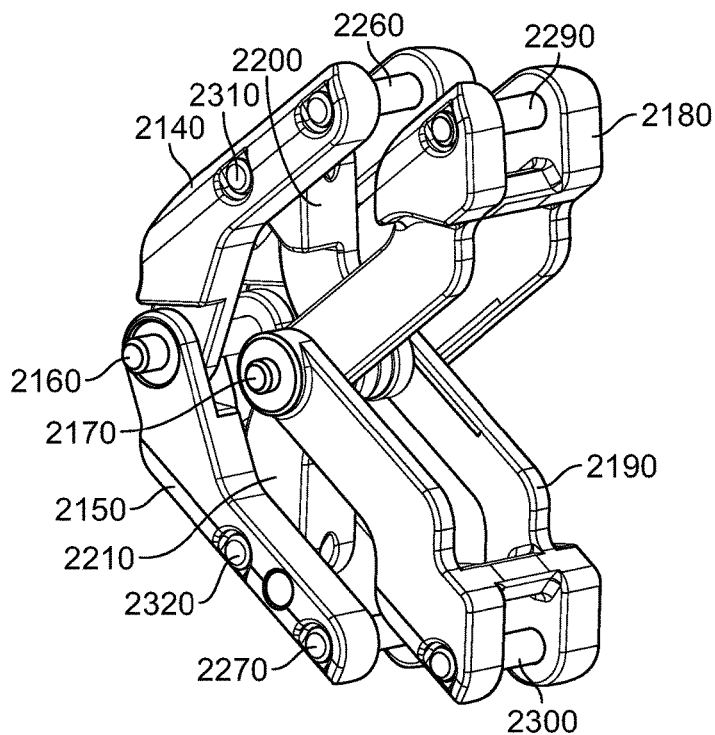
FIG. 36 is an elevated perspective view showing assembly of the toggles, parallel links, and drive links.
Figure 37:
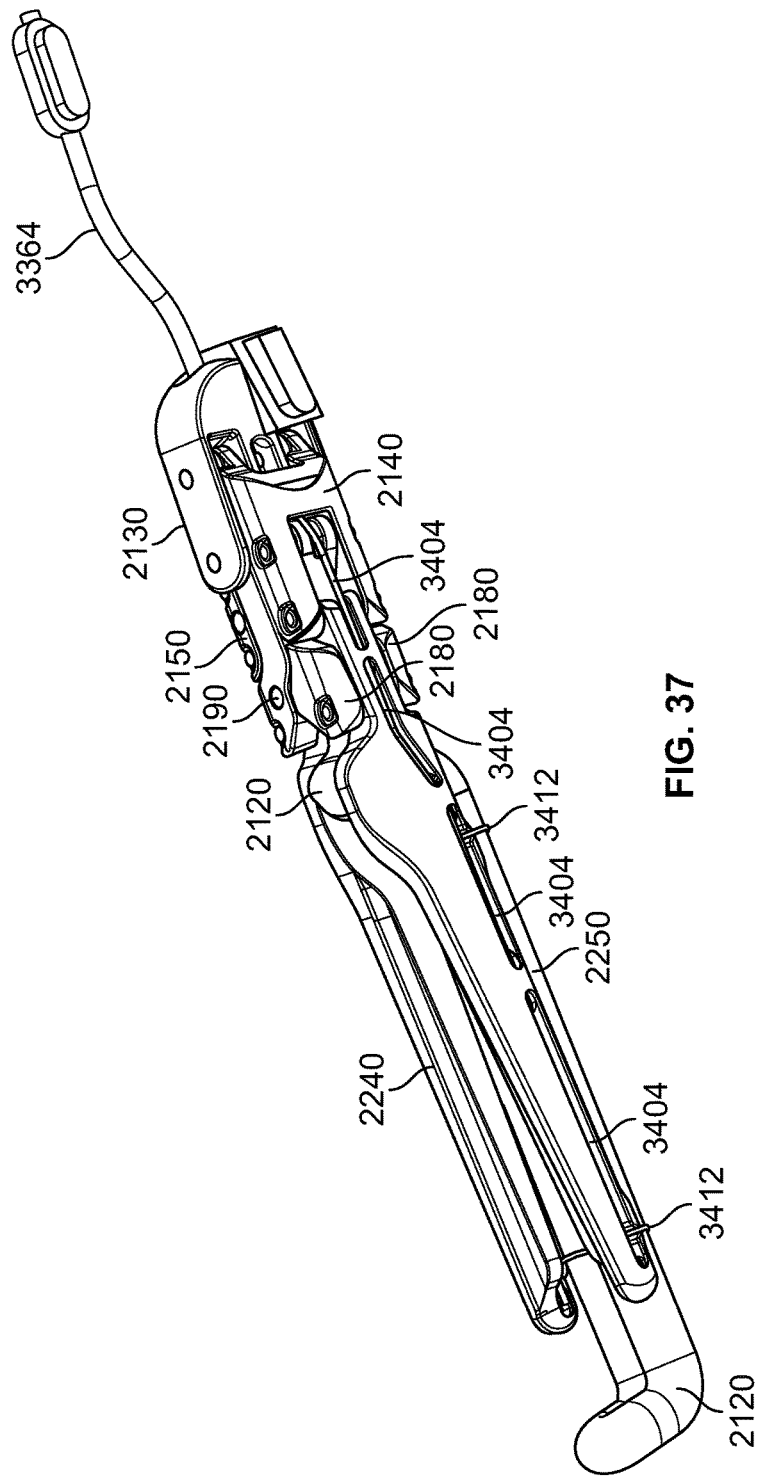
FIG. 37 is an elevated perspective view of an exemplary end effector having mounted thereto an occlusion clip in a closed position.
Figure 38:
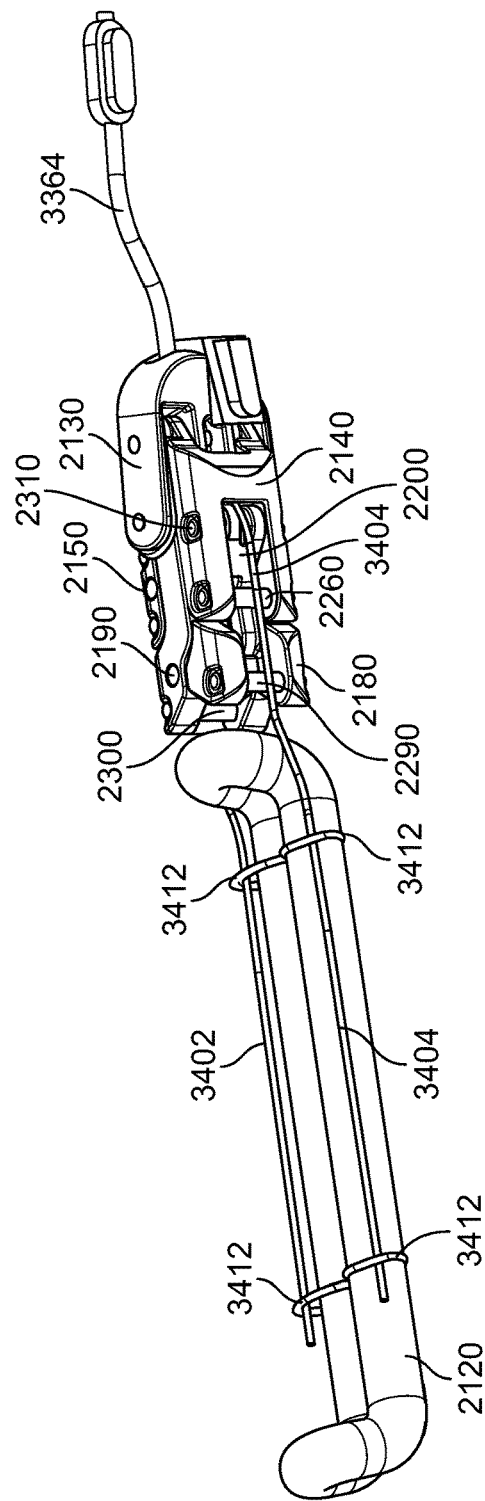
FIG. 38 is an elevated perspective view of the exemplary end effector and occlusion clip of FIG. 37 shown without repositionable jaws.
Figure 39:
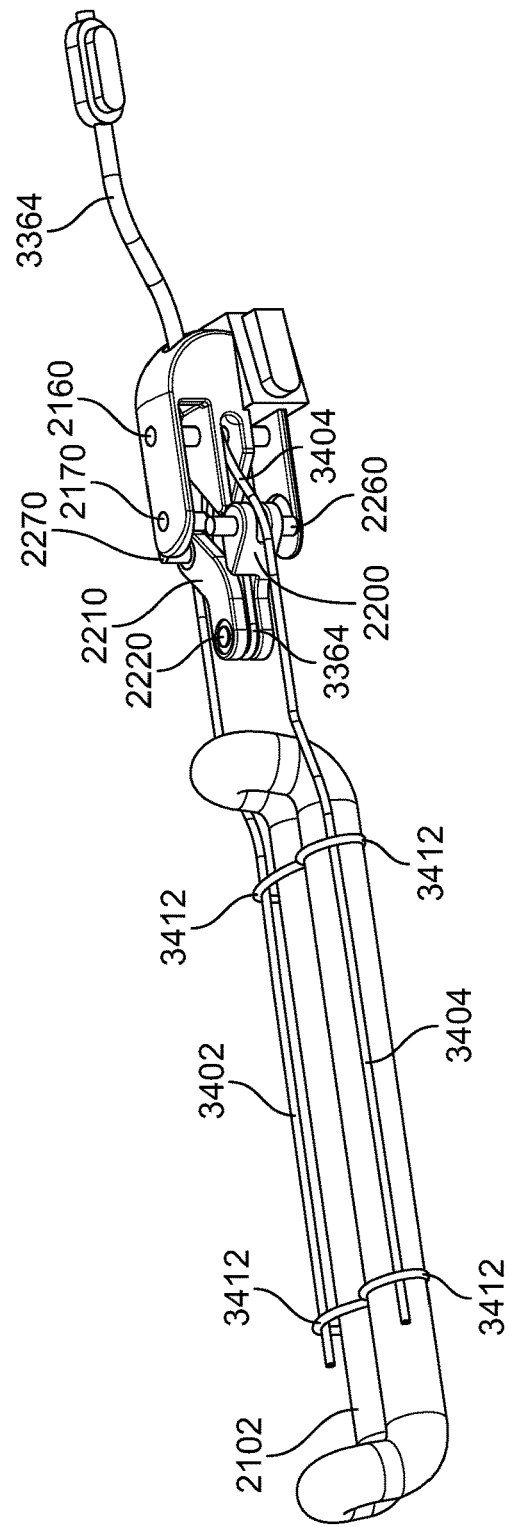
FIG. 39 is an elevated perspective view of the exemplary end effector and occlusion clip of FIG. 37 shown without repositionable jaws, first and second drive links, and first and second parallel links.

Each parallel link 2180, 2190 comprises a unitary structure including a pair of spaced apart heads 2700, 2702 that are angled approximately forty-five degrees with respect to corresponding longitudinal legs 2704, 2706. Near a base, the heads 2700, 2702 are joined to one another via a link 2710. In exemplary form, each head 2700, 2702 includes a tapered proximal end 2714, which is rounded at a far proximal tip, that includes a hole 2716 partially bounded by opposing interior and exterior planar surfaces 2718, 2720, as well as an arcuate exterior surface 2722. The hole 2716 has a cylindrical shape that is size to accommodate throughput of at least one of the seventh and eighth pin 2290, 2300 and allow rotational repositioning of a respective parallel link 2180, 2190 around a respective jaw 2240, 2250. Each head 2700, 2702 includes an S-shaped profile 2722 on one widthwise side that is configured to track an inverse S-shaped profile 2724 associated with an opposite side of the same head 2700, 2702. In this fashion, as shown in FIG. 31 when the parallel links 2180, 2190 are positioned adjacent one another and the jaws 2240, 2250 are least spaced apart, the S-shaped contour 2722 of one side of the first head 2700 of the first parallel link 2180 tracks the inverse S-shaped contour 2724 of a second side of the second head 2702 of the second parallel link 2190. Each head 2700, 2702 also includes a width that is roughly twice the width of the corresponding longitudinal legs 2704, 2706. In this fashion, the portion of heads 2700, 2702 with the inverse S-shaped profile 2724 is offset in a widthwise dimension from the corresponding longitudinal leg 2704, 2706.

The corresponding longitudinal legs 2704, 2706 extend parallel and spaced apart from one another in the widthwise direction. The only meaningful difference between the corresponding longitudinal legs 2704, 2706 is that the first longitudinal leg 2704 includes a widthwise offset 2728 that extends away from the second longitudinal leg 2706 proximate the rounded distal tip 2730. Each longitudinal leg includes parallel, planar inner and outer surfaces 2732, 2734. A first hole 2736 extends through the second longitudinal leg 2706 proximate the distal tip 2730, that is generally equidistantly spaced from the distal tip 2730 and corresponding upper and lower surfaces 2740, 2742. The first hole 2736 has a cylindrical shape and is configured to receive at least one of the second and third pins 2170, 2230 in order to allow the parallel links 2180, 2190 to rotate with respect to the linkage housing 2130. A second hole 2746 extends through the first longitudinal leg 2704 and offset 2728 proximate the distal tip 2730, that is generally equidistantly spaced from the distal tip 2730 and corresponding upper and lower surfaces 2740, 2742. The second hole 2746 has a cylindrical shape and is configured to receive at least one of the second and third pins 2170, 2230 in order to allow the parallel links 2180, 2190 to rotate with respect to the linkage housing 2130.

Referring to FIGS. 17-40, an exemplary assembly sequence for the exemplary end effector 2100 will now be described. Initially, the control and deployment wires 3164, 3402, 3404 are routed through the opening 2546 of the linkage housing 2130. At this point, the tilted uprights 2590, 2592 of the drive links 2140, 2150 are offset and aligned with one another to fit between the linkage housing 2130 proximate the orifices 2570. More specifically the holes 2610 of the tilted uprights 2590, 2592 are longitudinally aligned with the holes 2580 and the orifices 2570 of the linkage housing 2130 in order to receive the first pin 2160, which extends completely through the linkage housing and the drive links 2140, 2150.

The toggles 2200, 2210 are also mounted to a respective drive link 2140, 2150, as well as concurrently to the pulley 2220. Specifically, the through opening 2650 of the first toggle 2200 is oriented between and coaxially aligned with the openings 2622 extending through the first drive link 2140. When aligned, the ninth pin 2310 is inserted through the openings 2622, 2650 to mount the first toggle 2200 to the first drive link 2140. Similarly, the through opening 2650 of the second toggle 2210 is oriented between and coaxially aligned with the openings 2622 extending through the second drive link 2150. When aligned, the tenth pin 2320 is inserted through the openings 2622, 2650 to mount the second toggle 2210 to the second drive link 2150. The opposing ends of the toggles 2200, 2210 are mounted to opposing ends of the pulley 2220. More specifically, each toggle through opening 2646 receives a respective cylindrical lateral end of the pulley 2220 in order to rotationally mount the toggles 2200, 2210 to the pulley. At this time, the pulley 2220 is also mounted to the control wire 3364 so that repositioning of the control wire in tension is operative to reposition the pulley and correspondingly other components in order to move the jaws 2240, 2250 toward or away from one another in a parallel open/close fashion.

Each jaw 2240, 2250 is then mounted to a respective drive link 2140, 2150, and parallel link 2180, 2190. In exemplary form, a first of the openings 2662 of a respective jaw 2240, 2250 is aligned with a respective opening 2624 of a respective drive link 2140, 2150. After being aligned, a fifth pin 2260 and a respective sixth pin 2270 are inserted through the openings 2624, 2662 in order to pivotally mount a jaw 2240, 2250 to a respective drive link 2140, 2150. Similarly, a second of the openings 2664 of a respective jaw 2240, 2250 is aligned with a respective hole 2716 of a respective parallel link 2180, 2190. After being aligned, a seventh pin 2290 and a respective eighth pin 2300 is inserted through the openings 2664, 2716 in order to pivotally mount a jaw 2240, 2250 to a respective parallel link 2180, 2190. Also, the opposing ends of the parallel links 2180, 2190 are offset and aligned with one another to fit between the linkage housing 2130 proximate the orifices 2568. When aligned, second and third pins 2170, 2230 are mounted to individual ends of the parallel links 2180, 2190 and to the linkage housing 2130 to provide for pivotal motion between the parallel links and the linkage housing. Before, during, or after mounting the jaws 2240, 2250 to the drive links 2140, 2150 and the parallel links 2180, 2190, the deployment wires 3402, 3404 are respectively directed through openings 2674 of the jaws 2240, 2250.

The following comprises a description of exemplary processes for utilizing the exemplary end effector 2100. Initially, an incision is made on either the left or right side of the chest wall in an intercostal space that is appropriate for the desired angle of approach to a left atrial appendage (LAA). The incision may be made through the chest wall or through the abdomen (or through the back) as part of various procedures that include, without limitation, an open sternotomy, a left thoracotomy, a right thoracotomy, a left port, a right port, a subxiphoid approach, and a transdiaphragmatic approach. Post incision, a trocar (e.g., 10 mm or larger) may be inserted through the incision to extend into the thoracic cavity. In certain instances, it may be preferred to insufflate the thoracic space subsequent to trocar insertion using known techniques. Using at least one of the incision and trocar, surgical instruments are introduced into the thoracic space in order to perform a series of dissections, including dissection of the pericardium, to provide egress to the LAA. After having access to the LAA, the end effector 100 of the surgical tool 10 may be inserted into the thoracic cavity by way of the incision or trocar.

The end effector 2100 is passed through the trocar or incision and a robotic instrument or other means is used to navigate the end effector proximate the LAA. After navigating the LAA occlusion clip 2102 proximate the LAA, the occlusion clip 2102 is opened prior to deployment on the LAA.

Opening the LAA occlusion clip 2102 is carried out while a first robotic arm 4000 is coupled to the linkage housing 2130. More specifically, the first robotic arm 4000 includes a grasper 4010 comprised of a pair of repositionable, fenestrated jaws. In exemplary form, each opening of the fenestrated jaws is sized to circumscribe one of the elongated projections 2510 so that clamping of the fenestrated jaws clamps down on the trapezoidal block 2511 is operative to mount the end effector 2100 to the first robotic arm 4000 in a relatively secure position substantially free from significant play. While the first robotic arm 4000 is coupled to the end effector 2100, a second robotic arm 4020 and its grasper 4030 is repositioned to grasp an end of the control wire 3364 and thereafter moved away from the end effector 2100 to tension the control wire 3364, causing the end effector 2100 to further separate its jaws 2240, 2250 from one another and open the clip 2102. More specifically, tensioning the control wire 3364 is operative to reposition the pulley 2220 proximally. Because a respective cylindrical lateral end of the pulley 2220 is received in a through opening 2646 of a respective toggle 2200, 2210, when the pulley 2220 is repositioned proximally, so too are the toggles repositioned proximally (toward the linkage housing 2130) as well as rotating about an axis extending through the opening 2646. In particular, the proximal motion and rotation of the toggles 2200, 2210 operates to push against the first and second drive links 2140, 2150 via the ninth and tenth pins 2310, 2320 causing the drive links to move away from one another. But the connection between the first and second drive links 2140, 2150 and the linkage housing 2130, via the first pin 2160, causes the drive links to pivot with respect to the linkage housing about the first pin when the drive links are attempted to be moved away from one another via the motion of the toggles 2200, 2210.

The pivoting motion of the drive links 2140, 2150 is transferred to the jaws 2240, 2250 via the connection therebetween, facilitated by the fifth and sixth pins 2260, 2270. More specifically, the pivoting of the drive links 2140, 2150 away from one another causes the jaws 2240, 2250 to move away from one another. But the movement of the jaws 2240, 2250 away from one another is constrained by the connection of the jaws to the first and second parallel links 2180, 2190, which are themselves pivotally mounted to the linkage housing 2130. The additional constraint offered by the parallel links 2180 results in motion of the jaws 2240, 2250 that maintains the jaws in a generally parallel relationship as the jaws are moved from a closed position (adjacent one another with spacing to accommodate the clip 2102) to a fully open position (spaced away from one another to open the clip to a predetermined maximum extent necessary to position the clip on a LAA). This fully open position of the jaws 2240, 2250 coincides with the surface of the toggle connector portions 2640 contacting the first and second surfaces 2582, 2584 of the inner arms 2534, 2536, thus stopping further proximal and pivoting motion of the toggles 2200, 2210. In other words, the inner arms 2534, 2536 of the linkage housing 2130 operate to limit the travel of the toggles 2200, 2210, thereby setting the maximum spacing between the jaws 2240, 2250 in a fully open position.

As long as the jaws 2240, 2250 are attached to the occlusion clip 2102, the motion of the jaws results in corresponding motion of the occlusion clip. More specifically, when the jaws are in a closed position (see FIG. 18) and mounted to the occlusion clip 2102, the bias of the occlusion clip retains the jaws in the closed position. But when one wants to open the occlusion clip 2102 in anticipation of positioning the clip around a LAA, one must overcome the bias of the occlusion clip. In order to do this, the end effector 2100 incorporates structures that provide a mechanical advantage allowing the user to tension the control wire 3364, which as discussed in greater detail previously, ultimately causing the jaws 2240, 2250 to separate from one another and correspondingly separate the parallel beams of the occlusion clip 2102 from one another.

Post opening of the LAA occlusion clip 2102, the first robotic arm 4000 and grasper 4010, as well as the second robotic arm 4020 and its grasper 4030, are moved in concert to reposition the end effector 2100 and advance the clip 2102 over the distal tip of the LAA with the LAA passing between corresponding occlusion beams of the clip, stopping only upon reaching the base of the LAA. It should be noted that forceps may be used to grasp a portion of the LAA when positioning the LAA occlusion clip 2102. After the clip 2102 has been positioned at the base of the LAA, with the LAA interposing corresponding occlusion beam surfaces of the clip, the user may close the clip 2102 to sandwich the LAA between the occlusion surfaces.

Closing the LAA occlusion clip 2102 is also carried out by decreasing the tension on the control wire 3364, thereby allowing the bias of the clip 2102 to cause the jaws 2240, 2250 of the end effector 2100 moving closer to one another, thus sandwiching the clip around the LAA. More specifically, the second robotic arm 4020 and its grasper 4030 is repositioned toward the end effector 2100 to decrease the tension on the control wire 3364. By decreasing the tension of the control wire 3364, the bias of the clip 2102 dominates and causes jaws 2240, 2250 (which are mounted to the clip 2102) to be repositioned toward one another, coinciding with closing of the occlusion clip 2102. In exemplary form, the dominant biasing force of the occlusion clip 2102 is operative to reposition the jaws 2240, 2250, which in turn causes the first and second drive links 2140, 2150 to pivot toward one another, coinciding with the parallel links 2180, 2190 pivoting toward one another. Likewise, the toggles 2200, 2210 are pivoted and repositioned distally, as is the pulley 2220, ultimately leading to the component positions shown in FIG. 18.

After the occlusion clip 2102 is positioned about the LAA, various steps may be undertaken to ensure the entire periphery of a portion of LAA is sandwiched by the clip 2102 such as, without limitation, direct visual verification and utilization of a transesophageal echocardiogram. If any problems are determined with respect to the clip 2102 placement, the opening and closing clip sequence may be repeated to adjust the positioning of the clip with respect to the LAA. Upon closing the LAA occlusion clip 2102 around a periphery of a portion of the LAA, proximate the LAA base, as well as confirming the placement of the closed clip being operative to occlude the LAA, the surgeon may release the occlusion clip from the end effector 2100.

To release the clip 2102 from the end effector 2100, the second robotic arm 4020 and its grasper 4030 releases the control wire 3364 and grasps the deployment wires 3402, 3404. Post grasping of the deployment wires 3402, 3404, the second robotic arm 4020 and its grasper 4030 is moved away from the end effector 2100 to tension the deployment wires and reposition the deployment wires proximally, ultimately leading to discontinuing engagement with the suture loops 3412. When engagement between the suture loops 3412 and the deployment wires 3402, 3404 is discontinued, the occlusion clip 2102 is no longer fastened to the jaws 2240, 2250 (i.e., the jaws can be opened and closed without repositioning the clip). After disengagement between the occlusion clip 2102 and the end effector 2100, the end effector may be removed from the cardiac space, as well as the deployment wires 3402, 3404 using the first and second robotic arms 4000, 4020.

Removal of the end effector 2100 from the patient's body may be controlled by repositioning of the first robotic arm 4000. Because the end effector 2100 is open-ended, there is no need to reposition the end effector upward along the LAA because the end effector can be withdrawn laterally, thus reducing the potential for contact between the end effector and the LAA. In other words, the end effector 2100 may be removed from around the LAA without having a tip of the LAA passing between the jaws 2240, 2250. As part of removing the end effector 2100 from the cardiac and thoracic space, the first robotic arm 4000 may be withdrawn from the patient's body cavity via the incision or trocar while coupled to the end effector 2100.

Following from the above description and invention summaries, it should be apparent to those of ordinary skill in the art that, while the methods and apparatuses herein described constitute exemplary embodiments of the present invention, it is to be understood that the inventions contained herein are not limited to the above precise embodiment and that changes may be made without departing from the scope of the invention as defined by the following proposed points of novelty. Likewise, it is to be understood that it is not necessary to meet any or all of the identified advantages or objects of the invention disclosed herein in order to fall within the scope of the invention, since inherent and/or unforeseen advantages of the present invention may exist even though they may not have been explicitly discussed herein.

What is claimed is:

1. A method of deploying an occlusion clip comprising:
   inserting an open-ended occlusion clip with dual terminal ends removably mounted to an end effector through at least one of an incision and a trocar, the end effector devoid of a handle control, the open-ended occlusion clip and the end effector operatively coupled to one another prior to insertion into and through at least one of the incision and the trocar;
   repositioning the end effector using a first robotic tool to reposition the open-ended occlusion clip so the open-ended occlusion clip is interposed by a portion of a left atrial appendage between a base and a tip of the left atrial appendage without needing to pass a tip of the left atrial appendage between opposing clamping surfaces of the open-ended occlusion clip and without needing to pierce the left atrial appendage;
   clamping the left atrial appendage with the open-ended occlusion clip to cause necrosis to the left atrial appendage by repositioning a second robotic tool with respect to the end effector;
   discontinuing operative coupling between the open-ended occlusion clip and the end effector; and,
   withdrawing the end effector through at least one of the incision and the trocar.

2. The method of claim 1, wherein the inserting step occurs during at least one of an open sternotomy, a left thoracotomy, a right thoracotomy, a left port procedure, a right port procedure, a subxiphoid approach, and a transdiaphragmatic approach.

3. The method of claim 1, further comprising insufflating a thoracic space prior to the inserting step.

4. The method of claim 1, further comprising:
   making an incision as part of a procedure comprising at least one of an open sternotomy, a left thoracotomy, a right thoracotomy, a left port procedure, a right port procedure, a subxiphoid approach, and a transdiaphragmatic approach; and,
   introducing a trocar through the incision.

5. The method of claim 1, wherein a first line is operatively coupled the end effector.

6. The method of claim 5, wherein:
   the end effector includes a first jaw operatively coupled to the open-ended occlusion clip;
   the end effector includes a second jaw operatively coupled to the open-ended occlusion clip; and,
   repositioning the end effector to reposition the open-ended occlusion clip includes tensioning the first line to cause increased spacing between the first jaw and the second jaw.

7. The method of claim 1, further comprising grasping the left atrial appendage concurrent with repositioning the end effector deployment device to reposition the occlusion clip so the open end of the open-ended occlusion clip is interposed by the portion of the left atrial appendage.

8. The method of claim 1, further comprising repeating the repositioning and clamping steps prior to the disengaging step.

9. The method of claim 1, further comprising confirming a clamping position of the open-ended occlusion clip is operative to cause necrosis to the left atrial appendage using at least one of visualization and a transesophageal echocardiogram.

10. The method of claim 1, wherein:
    the inserting step includes inserting the open-ended occlusion clip and the end effector through the trocar;
    the withdrawing step includes withdrawing the end effector through the trocar; and,
    the trocar comprises a twelve millimeter or less diameter cross-section.

11. A method of deploying a necrosis clip comprising:
    inserting an open-ended necrosis clip having dual terminal ends, removably mounted to an end effector having repositionable jaws, through at least one of an incision and a trocar, the open-ended necrosis clip biased to a clamping position;
    repositioning the end effector to counteract a bias of the open-ended necrosis clip, via repositioning a first robotic tool, and repositioning the open-ended necrosis clip to a tissue insertion position where less than a full bias of the open-ended necrosis clip would be applied to an inserted left atrial appendage;
    spatially repositioning the end effector using a second robotic arm while the open-ended necrosis clip is in the tissue insertion position so a portion of the left atrial appendage between a base and a tip of the left atrial appendage interposes opposing clamping surfaces of the open-ended necrosis clip without having a tip of the left atrial appendage interpose the open-ended necrosis clip; and,
    repositioning the end effector, via repositioning the first robotic tool, to reposition the open-ended necrosis clip from the tissue insertion position to a tissue clamping position where the full bias of the open-ended necrosis clip is applied to the portion of the left atrial appendage tissue to initiate necrosis of the left atrial appendage tip.

12. A method of deploying a necrosis clip comprising:
    inserting a necrosis clip removably mounted to an end effector through at least one of an incision and a trocar, the end effector devoid of a handle control, the necrosis clip and the end effector operatively coupled to one another prior to insertion into and through at least one of the incision and the trocar;
    repositioning the end effector using a first robotic tool to reposition the necrosis clip so the necrosis clip is interposed by a portion of a left atrial appendage without needing to pierce the left atrial appendage;

clamping the left atrial appendage with the necrosis clip to cause necrosis to the left atrial appendage by repositioning a second robotic tool with respect to the end effector while the end effector is coupled to the first robotic tool, the second robotic tool coupled to a first line of the end effector operatively coupled to the necrosis clip so that movement of the first line with respect to the end effector causes closing motion of the necrosis clip;

discontinuing operative coupling between the necrosis clip and all of the end effector, the first robotic tool, and the second robotic tool; and, withdrawing the end effector through at least one of the incision and the trocar.

13. The method of claim 12, wherein the inserting step occurs during at least one of an open sternotomy, a left thoracotomy, a right thoracotomy, a left port procedure, a right port procedure, a subxiphoid approach, and a transdiaphragmatic approach.

14. The method of claim 12, further comprising insufflating a thoracic space prior to the inserting step.

15. The method of claim 12, further comprising:
making an incision as part of a procedure comprising at least one of an open sternotomy, a left thoracotomy, a right thoracotomy, a left port procedure, a right port procedure, a subxiphoid approach, and a transdiaphragmatic approach; and,
introducing a trocar through the incision.

16. The method of claim 12, wherein:
the end effector includes a first jaw operatively coupled to the necrosis clip;
the end effector includes a second jaw operatively coupled to the necrosis clip; and,
repositioning the end effector to reposition the necrosis clip includes:
the first robotic tool being coupled to the end effector;
using the second robotic tool to cause movement of the first line with
respect to the end effector thereby causing opening motion of the necrosis clip.

17. The method of claim 12, further comprising grasping the left atrial appendage concurrent with repositioning the end effector deployment device to reposition the necrosis clip so the necrosis clip is interposed by the portion of the left atrial appendage.

18. The method of claim 12, further comprising repeating the repositioning and clamping steps prior to the disengaging step.

19. The method of claim 12, further comprising confirming a clamping position of the necrosis clip is operative to cause necrosis to the left atrial appendage using at least one of visualization and a transesophageal echocardiogram.

20. The method of claim 12, wherein:
the inserting step includes inserting the necrosis clip and the end effector through the trocar;
the withdrawing step includes withdrawing the end effector through the trocar; and,
the trocar comprises a twelve millimeter or less diameter cross-section.

* * * * *